US009585947B2

(12) United States Patent
Lycke

(10) Patent No.: US 9,585,947 B2
(45) Date of Patent: Mar. 7, 2017

(54) MUTANT CTAI FUSION PROTEIN FOR TREATMENT OF ALLERGY AND AUTOIMMUNE DISEASE

(75) Inventor: Nils Lycke, Vastra Frolunda (SE)

(73) Assignee: TOLERANZIA AB, Gothenburg (SE)

( * ) Notice: Subject to any disclaimer, the term of this patent is extended or adjusted under 35 U.S.C. 154(b) by 0 days.

(21) Appl. No.: 13/638,069

(22) PCT Filed: Oct. 28, 2011

(86) PCT No.: PCT/SE2011/000191
§ 371 (c)(1),
(2), (4) Date: Sep. 28, 2012

(87) PCT Pub. No.: WO2012/057671
PCT Pub. Date: May 3, 2012

(65) Prior Publication Data
US 2013/0022634 A1      Jan. 24, 2013

(30) Foreign Application Priority Data

Oct. 28, 2010 (SE) .................................... 1051122

(51) Int. Cl.
*A61K 39/00*   (2006.01)
*A61K 39/35*   (2006.01)
*A61K 39/39*   (2006.01)

(52) U.S. Cl.
CPC .......... *A61K 39/0008* (2013.01); *A61K 39/35* (2013.01); *A61K 39/39* (2013.01); *A61K 2039/6037* (2013.01)

(58) Field of Classification Search
None
See application file for complete search history.

(56) References Cited

U.S. PATENT DOCUMENTS

| 5,917,026 A | 6/1999 | Lowenadler |
| 5,939,400 A | 8/1999 | Steinman |

FOREIGN PATENT DOCUMENTS

| WO | 9219265 A1 | 11/1992 |
| WO | 9746253 | 12/1997 |
| WO | 0053019 | 9/2000 |
| WO | 03045316 | 6/2003 |
| WO | 2004047734 | 6/2004 |
| WO | 2009078796 A1 | 6/2009 |

OTHER PUBLICATIONS

Wadell, A.K. and Lycke, N. FASEB J. 2001; 15(5):A1230.*
Hasselberg, A., et al. J. Immunol. 2010;184:2776-2784.*
Kap, Y.S., et al. Clin. Exp. immunol. 2014; E Pub.*
Ampapathi R.S. et. al., "Order-disorder-order transitions mediate the activation of cholera toxin", J. Mol. Biol., 2008, vol. 377, pp. 748-760; p. 757, col. 1, paragraph 3.

Hasselberg, A., et al., "Role of CTA1R7K-COL-DD as a Novel Therapeutic Mucosal Tolerance-Inducing Vector for Treatment of Collagen-Induced Arthiritis", Arthritis & Rheumatism, vol. 60, No. 6, pp. 1672-1682, Jun. 2009.
Ågren et al., "Adjuvanticity of the Cholera Toxin A1-Based Gene Fusion Protein, CTA1-DD, is Critically Dependent on the ADP-Ribosyltransferase and Ig-Binding Activity", The Journal of Immunology, vol. 162, 1999, pp. 2432-2440.
Ågren et al., "Genetically Engineered Nontoxic Vaccine Adjuvant that Combines B Cell Targeting with Immunomodulation by Cholera Toxin A1 Subunit", The Journal of Immunology, vol. 158, 1997, pp. 3936-3946.
Akbari et al., "Role of Regulatory T Cells in Allergy and Asthma", Current Opinion in Immunology, vol. 15, 2003, pp. 627-633.
Akhiani et al., "The Nontoxic CTA1-DD Adjuvant Enhances Protective Immunity Against Helicobacter Pylori Infection Following Mucosal Immunization", Scandinavian Journal of Immunology, vol. 63, pp. 97-105.
Appelbaum, "Haematopoietic Cell Transplantation as Immunotherapy", Nature, vol. 411, May 17, 2001, pp. 385-389.
Ausubel et al., "Current Protocols in Molecular Biology", Wiley, John & Sons, Incorporated, Edition 1, Nov. 14, 1988.
Brocke et al., "Treatment of Experimental Encephalomyelitis with a Peptide Analogue of Myelin Basic Protein", Nature, vol. 379, Jan. 25, 1996, pp. 343-346.
Chen et al., "Peripheral Deletion of Antigen-Reactive T Cells in Oral Tolerance", Nature, vol. 376, Jul. 13, 1995, pp. 177-180.
Cherwinski et al., "Two Types of Mouse Helper T Cell Clone", J Exp Med, vol. 156, Nov. 1987, pp. 1229-1244.
Critchfield et al., "T Cell Deletion in High Antigen Dose Therapy of Autoimmune Encephalomyelitis", Science, vol. 263, Feb. 25, 1994, pp. 1139-1143.
Delaleu et al., "Inhibition of Experimental Sjögren's Syndrome Through Immunization with Hsp60 and its Peptide Amino Acids 437-460". Arthritis & Rheumatism, vol. 58, No. 8, Aug. 2008, pp. 2318-2328.
Eliasson et al., "CTA1-M2e-DD: A Novel Mucosal Adjuvant Targeted Influenza Vaccine", Vaccine, vol. 26, 2008, pp. 1243-1252.
Fiorentino et al., "Two Types of Mouse T Helper Cell", J Exp Med, vol. 170, Dec. 1989, pp. 2081-2095.
Fox, "Biological Therapies: A Novel Approach to the Treatment of Autoimmune Disease", The American Journal of Medicine, vol. 99, Jul. 1995, pp. 82-88.
Freytag et al., "Bacterial Toxins as Mucosal Adjuvants", Department of Microbiology and Immunology, vol. 236, 1999, pp. 215-236.
Fujihashi et al., "A Dilemma for Mucosal Vaccination: Efficacy Versus Toxicity using Enterotoxin-based Adjuvants", Vaccine, vol. 20, 2002, pp. 2431-2438.

(Continued)

*Primary Examiner* — Gerald R Ewoldt
(74) *Attorney, Agent, or Firm* — Birch, Stewart, Kolasch & Birch, LLP

(57) ABSTRACT

The present invention provides improved methods and compositions for treating and preventing autoimmune and allergic diseases. More specifically, the invention relates to new immunomodulating complexes that are fusion proteins comprising a mutant subunit of the A1-subunit of the cholera toxin (CTA1), a peptide capable of binding to a specific cellular receptor, and one or more epitopes associated with an autoimmune or allergic disease. In the mutant CTA1 subunit, the amino acids corresponding to the amino acid 7, arginine, and amino acid 187, cysteine, in the native CTA1 have been replaced.

3 Claims, 5 Drawing Sheets

(56) References Cited

OTHER PUBLICATIONS

Garside et al., "Machanisms of Oral Tolerance", Critical Reviews in Immunology, vol. 17, 1997, pp. 119-137.
Genain et al., "Allergic Encephalomyelitis in Common Marmosets: Pathogenesis of a Multiple Sclerosis-Like Lesion", Methods, vol. 10. Iss. 3, Dec. 1996, pp. 420-434.
Gershwin et al., "Primary Biliary Cirrhosis: An Orchestrated Immune Response Against Epithelial Cells", Immunological Reviews, vol. 174, 2000, pp. 210-225.
Giuliani et al., "Mucosal Adjuvanticity and Immunogenicity of LT R 72, a Novel Mutant of *Escherichia coli* Heat-Labile Enterotoxin with Partial Knockout of ADP-Ribosyltransferase Activity". J Exp Med, vol. 187, No. 7, Apr. 6, 1998, pp. 1123-1132.
Glück et al., "Safety and Immunogenicity of Intranasally Administered Inactivated Trivalent Virosome-Formulated Influenza Vaccine Containing *Escherichia coli* Heat-Labile Toxin as a Mucosal Adjuvent", The Journal of Infectious Diseases, vol. 181, 2000, pp. 1129-1132.
Glueck, "Pre-clinical and Clinical Investigation of the Safety of a Novel Adjuvant for Intranasal Immunization", Vaccine, vol. 20, 2002, pp. S42-S44.
Gumanovskaya et al., "Intravenous Tolerization with Type II Collagen Induces Interleukin-4-and Interleukin-10-producing CD4 T Cells", Immunology, vol. 97, 1999, pp. 466-473.
Haneji et al., "Identification of α-Fodrin as a Candidate Autoantigen in Primary Sjögren's Syndrome", Science, vol. 275, Apr. 25, 1997, pp. 604-607.
Holmgren et al., "Strategies for the Induction of Immune Responses at Mucosal Surfaces Making use of Cholera Toxin B Subunit as Immunogen, Carrier, and Adjuvant", Am J Trop Med Hyg, vol. 50, No. 5, 1994, pp. 42-54.
Holz et al., "Myelin-Associated Oligodendrocylic Basic Protein: Identification of an Encephalitogenic Epitope and Association with Multiple Sclerosis", The Journal of Immunology, vol. 164, 2000, pp. 1103-1109.
Hufnagl et al., "Airway Inflammation Induced after Allergic Poly-Sensitization can be Prevented by Mucosal but not by Systemic Administration of Poly-Pepties", Clinical & Experimental Allergy, vol. 38, Iss. 7, Jul. 2008, pp. 1192-1202.
Hurtenbach et al., "Prevention of Autoimmune Diabetes in Non-Obese Diabetic Mice by Treatment with a Class II Major Histocompatibility Complex-blocking Peptide", J Exp Med, vol. 177, May 1983, pp. 1499-1504.
Infante-Duarte et al., "Microbial Lipopeptides Induce the Production of IL-17 in Th Cells", J Immunol, vol. 165, 2000, pp. 6107-6115.
Jacobson et al., "Epidemiology and Estimated Population Burden of Selected Autoimmune Diseases in the United States", Clin Immunol Immunopathol, vol. 84, No. 3, 1997, pp. 223-243.
Kerlero de Rosbo et al., "Predominance of the Autoimmune Response to Myelin Oligodendrocyte Glycoprotein (MOG) in Multiple Sclerosis Reactivity to the Extracellular Domain of MOG is Directed Against Three Main Regions", Eur J Immunol, vol. 27, 1997, pp. 3059-3069.
Kim et al., "Oral Administration of Collagen Conjugated with Cholera Toxin Induces Tolerance to Type II Collagen and Suppresses Chondritis in an Animal Model of Autoimmune Ear Disease", Annals of Otology Rhinology & Laryngology, vol. 110, No. 7, Jul. 2001, pp. 646-654.
Lycke, "From Toxin to Adjuvant: Basic Mechanisms for the Control of Mucosal Iga Immunity and Tolerance", Immunology Letters, vol. 97, 2005, pp. 193-198.
Mackay et al., "The Peculiar Autoimmunity of Primary Biliary Cirrhosis", Immunological Reviews, vol. 174, 2000, pp. 226-237.
Marrack et al., "Autoimmune Disease: Why and Where it Occurs", Nature Medicine, vol. 7. No. 8, Aug. 2001, pp. 899-905.
Mavragani et al., "Sjögren's Syndrome: Autoantibodies to Cellular Antigens", Int Arch Allergy Immunol, vol. 123, 2000, pp. 46-57.
McKown et al., "Lack of Efficacy of Oral Bovine Type II Collagen Added to Exisiting Therapy in Rheumatoid Arthritis", Arthritis & Rheumatism, vol. 42, No. 6, Jun. 1999, pp. 1204-1208.
Meinl et al., "Myelin Basic Protein-Specific T Lymphocyte Repertoire in Multiple Sclerosis" J Clin Invest, vol. 92, Dec. 1993, pp. 2633-2643.
Mills, "Regulatory T Cells: Friend or Foe in Immunity to Infection?", Nature Reviews, vol. 4, Nov. 2004, pp. 841-855.
Moreland et al., "Management of Rheumatoid Arthritis: The Historical Context", J Rheumatol, vol. 28, 2001, pp. 1431-1452.
Mosmann et al., "Two Types of Murine Helper T Cell Clone", The Journal of Immunology, vol. 136, No. 7, Apr. 1, 1986, pp. 2348-2357.
Mullis et al., "[21] Specific Synthesis of DNA in Vitro via a Polymerase-Catalyzed Chain Reaction", Methods in Enzymology, vol. 155, 1987, pp. 335-350.
Mutsch et al., "Use of the Inactivated Intranasal Influenza Vaccine and the Risk of Bell's Palsy in Switzerland", N Engl J Med, vol. 350, 2004, pp. 896-903.
Nussenblatt et al., "Treatment of Uveitis by Oral Administration of Retinal Antigens: Results of a Phase I/II Randomized Masked Trial", American Journal of Ophthalmology, vol. 123, 1997, pp. 583-592.
Oksenberg et al. "Selection for T-cell Receptor Vβ-Dβ-Jβ Gene Rearrangements with Specificity for a Myelin Basic Protein Peptide in Brain Lesions of Multiple Sclerosis", Nature, vol. 362, Mar. 4, 1993, pp. 68-70.
Pozzilli et al., "Oral Insulin and the Induction of Tolerance in Man: Reality or Fantasy?", Diabetes Metab Res Rev, vol. 16, 2000, pp. 306-307.
Ramshaw et al., "DNA Vaccines for the Treatment of Autoimmune Disease". Immunology and Cell Biology, 1997, vol. 75, pp. 409-413.
Rappuoli et al., "Structure and Mucosal Adjuvanticity of Cholera and *Escherichia coli* Heat-Labile Enterotoxins", Viewpoint Immunology Today, vol. 20, No. 11, Nov. 1999, pp. 493-500.
Ricchiuti et al., "Epitope Mapping with Synthetic Peptides of 52-kD SSA/Ro Protein Reveals Heterogeneous Antibody Profiles in Human Autoimmune Sera", Clin Exp Immunol, vol. 95, 1994, pp. 397-407.
Routsias et al., "Epitope Mapping of the Ro/SSA60KD Autoantigen Reveals Disease-Specific Antibody-Binding Profiles", European Journal of Clinical Investigation, vol. 26, Iss. 6, Jun. 1996, pp. 514-521.
Sanger et al., DNA Sequencing with Chain-Terminating Inhibitors, Proc Natl Acad Sci, vol. 74, No. 12, Dec. 1977, pp. 5463-5467.
Scofield et al., "Immunization with Short Peptides from the 60-kDa Ro Antigen Recapitulates the Serological and Pathological Findings as well as the Salivary Gland Dysfunction of Sjögren's Syndrome", J Immunol, vol. 175, 2005, pp. 8409-8414.
Soriani et al., "Contribution of the ADP-Ribosylating and Receptor-Binding Properties of Cholera-Like Enterotoxins in Modulating Cytokine Secretion by Human Intestinal Epithelial Cells", Microbiology, vol. 148, 2002, pp. 667-676.
Tarkowski et al., "Treatment of experimental autoimmune arthritis by nasal administration of a type II collagen-cholera toxoid conjugate vaccine", Arthritis & Rheumatism, vol. 42, No. 8, Aug. 1999, pp. 1628-1634.
Trentham et al., "Effects of Oral Administration of Type II Collagen on Rheumatoid Arthritis", Science, vol. 261, Sep. 24, 1993, pp. 1727-1730.
Tzioufas et al., "Fine Specificity of Autoantibodies to La/SSB: Epitope Mapping, and Characterization", Clin Exp Immunol, vol. 108, No. 2, May 1997, pp. 191-198.
Van Snick et al., "Cloning and Characterization of a cDNA for a New Mouse T Cell Growth Factor (P40)", J Exp Med, vol. 169, Jan. 1989, pp. 363-368.
Vandenbark et al., "Immunization with a Synthetic T-Cell Receptor V-Region Peptide Protects Against Experimental Autoimmune Encephalomyelitis", Nature, vol. 341, Oct. 12, 1989, pp. 541-544.
Von Herrath, "Bystander Suppression Induced by Oral Tolerance", Res Immunol, vol. 148, 1997, pp. 541-554.

(56) References Cited

OTHER PUBLICATIONS

Vrtala et al., "Strategies for Converting Allergens into Hypoallergenic Vaccine Candidates", Methods, vol. 32, 2004, pp. 313-320.

Waisman et al., "Suppressive Vaccination with DNA Encoding a Variable Region Game of the T-Cell Receptor Prevents Autoimmune Encephalomyelitis and Activates Th2 Immunity", Nat Med, vol. 2, No. 8, Aug. 1996, pp. 899-905.

Weiner et al., "Oral Tolerance: Immunologic Mechanisms and Treatment of Animal and Human Organ-Specific Autoimmune Disease by Oral Administration of Autoantigens", Ann Rev Immunol, vol. 12, 1994, pp. 809-837.

Weiner, "Oral Tolerance: Immunol Mechanisms and Treatment of Autoimmune Diseases", Review Immunology Today, vol. 18, No. 7, Jul. 1997, p. 335.

Wheeler et al., "Heterogeneity of a Major Allergen from Olive (Olea Europea) Pollen", Molecular Immunology, vol. 27, No. 7, 1990, pp. 631-636.

Wiedermann, "Prophylaxis and Therapy of Allergy by Mucosal Tolerance Induction with Recombinant Allergens or Allergen Constructs", Current Drug Targets—Inflammation & Allergy, vol. 4, 2005, pp. 577-583.

Wildbaum et al., "A Targeted DNA Vaccine Augments the Natural Immune Response to Self TNf-$\alpha$ and Suppresses Ongoing Adjuvant Arthritis", J Immunol, vol. 155, 2000, pp. 5860-5866.

Wildbaum et al., "A Targeted DNA Vaccine Encoding Fas Ligand Defines its Dual Role in the Regulation of Experimental Autoimmune Encephalomyelitis", J Clin Invest, vol. 106, No. 5, Sep. 2000, pp. 671-679.

Wucherpfennig et al., "Recognition of the Immunodominant Myelin Basic Protein Peptide by Autoantibodies and HLA-DR2-restricted T Cell Clones from Multiple Sclerosis Patients", J Clin Invest, vol. 100, No. 5, Sep. 1997, pp. 1114-1122.

Yamamoto et al., "Mutants in the ADP-Ribosyltransferase C Left of Cholera Toxin Lack Diarrheagenicity but Retain Adjuvanticity", J Exp Med, vol. 185, No. 7, Apr. 7, 1997, pp. 1203-1210.

Youssef et al., "C-C Chemokine-Encoding DNA Vaccines Enhance Breakdown of Tolerance to their Gene Products and Treat Ongoing Adjuvant Arthritis", J Clin Invest, vol. 106, No. 3, Aug. 2000, pp. 361-371.

\* cited by examiner

A

B

MUTANT CTA1 FUSION PROTEIN FOR TREATMENT OF ALLERGY AND AUTOIMMUNE DISEASE

FIELD OF THE INVENTION

The present invention relates to the fields of immunology and medicine. The present invention provides improved methods and compositions for treating and preventing autoimmune and allergic diseases. More specifically, the invention relates to new immunomodulating complexes that are fusion proteins comprising mutant subunits of bacterial endotoxins, a peptide capable of binding to a specific cellular receptor, and one or more autoantigenic or allergy-provoking epitopes associated with an autoimmune or allergic disease.

BACKGROUND

Autoimmune Disease and Modulation of the Immune Response

Autoimmune disease is any disease caused by immune cells that become misdirected at healthy cells and/or tissues of the body. Autoimmune disease affects 3% of the U.S. population, and likely a similar percentage of the industrialized world population (Jacobson et al., Clin Immunol Immunopathol 84: 223-43, 1997). Autoimmune diseases are characterized by T and B lymphocytes that aberrantly target self-proteins, -polypeptides, -peptides, and/or other self-molecules, causing injury and or malfunction of an organ, tissue, or cell-type within the body (for example, pancreas, brain, thyroid or gastrointestinal tract) to cause the clinical manifestations of the disease (Marrack et al., Nat Med 7: 899-905, 2001). Autoimmune diseases include diseases that affect specific tissues, as well as diseases that can affect multiple tissues. For some diseases, this may, in part, depend on whether the autoimmune responses are directed to an antigen confined to a particular tissue, or to an antigen that is widely distributed in the body. The characteristic feature of tissue-specific autoimmunity is the selective targeting of a single tissue or individual cell type. Nevertheless, certain autoimmune diseases that target ubiquitous self-proteins can also affect specific tissues. For example, in polymyositis, the autoimmune response targets the ubiquitous protein histidyl-tRNA synthetase, yet the clinical manifestations primarily involve autoimmune destruction of muscle.

The immune system employs a highly complex mechanism designed to generate responses to protect mammals against a variety of foreign pathogens, while at the same time preventing responses against self-antigens. In addition to deciding whether to respond (antigen specificity), the immune system must also choose appropriate effector functions to deal with each pathogen (effector specificity). A cell critical in mediating and regulating these effector functions is the $CD4^+$ T cell. Furthermore, it is the elaboration of specific cytokines from $CD4^+$ T cells that appears to be the major mechanism by which T cells mediate their functions. Thus, characterizing the types of cytokines made by $CD4^+$ T cells as well as how their secretion is controlled is extremely important in understanding how the immune response is regulated.

The characterization of cytokine production from long-term mouse $CD4^{+-}$ T cell clones was first published more than 20 years ago (Mosmann et al., J Immunol 136: 2348-2357, 1986). In these studies, it was shown that CD4+ T cells produced two distinct patterns of cytokine production, which were designated T helper 1 (Th1) and T helper 2 (Th2). Th1 cells were found to produce interleukin-2 (IL-2), interferon-$\gamma$ (IFN-$\gamma$) and lymphotoxin (LT), while Th2 clones predominantly produced IL-4, IL-5, IL-6, and IL-13 (Cherwinski et al., J Exp Med 169:1229-1244, 1987). Somewhat later, additional cytokines, IL-9 and IL-10, were isolated from Th2 clones (Van Snick et al., J Exp Med 169: 363-368, 1989) (Fiorentino et al., J Exp Med 170:2081-2095, 1989). Finally, additional cytokines, such as IL-3, granulocyte macrophage colony-stimulating factor (GM-CSF), and tumor necrosis factor-$\alpha$ (TNF-$\alpha$) were found to be secreted by both Th1 and Th2 cells. Recently, it was reported that CD4+ T cells isolated from the inflamed joints of patients with Lyme disease contain a subset of IL-17-producing CD4+ T cells that are distinct from Th1 and Th2 (Infante-Duarte et al., J. Immunol 165:6107-6115, 2000). These IL-17-producing CD4+ T cells are designated Th17. IL-17, a proinflammatory cytokine predominantly produced by activated T cells, enhances T cell priming and stimulates fibroblasts, endothelial cells, macrophages, and epithelial cells to produce multiple proinflammatory mediators, including IL-1, IL-6, TNF-α, NOS-2, metalloproteases, and chemokines, resulting in the induction of inflammation. IL-17 expression is increased in patients with a variety of allergic and autoimmune diseases, such as RA, MS, inflammatory bowel disease (IBD), and asthma, suggesting the contribution of IL-17 to the induction and/or development of such diseases.

There is ample evidence showing that suppressor T cells, now called regulatory T cells (Treg cells), suppress autoreactive T cells as an active mechanism for peripheral immune tolerance. Thus far, it is firmly established that Treg cells can be divided into two different subtypes, namely natural (or constitutive) and inducible (or adaptive) populations according to their origins (Mills, Nat Rev Immunol 4:841-855, 2004). In addition, a variety of Treg cell subsets have been identified according to their surface markers or cytokine products, such as CD4+ Treg cells (including natural CD4+ CD25+ Treg cells, IL-10-producting Tr1 cells, and TGF-β-producing Th3 cells), CD8+ Treg cells, Veto CD8+ cells, γδ T cells, NKT (NK1.1+CD4−CD8−) cells, NK1.1−CD4−CD8− cells, etc. Accumulating evidence has shown that naturally occurring CD4+CD25+ Treg cells play an active role in down-regulating pathogenic autoimmune responses and in maintaining immune homeostasis (Akbari et al., Curr Opin Immunol 15:627-633, 2003).

Autoimmune disease encompasses a wide spectrum of diseases that can affect many different organs and tissues within the body (see, e.g., Paul, W. E. (1999), Fundamental Immunology, Fourth Edition, Lippincott-Raven, New York.)

Current therapies for human autoimmune disease include glucocorticoids, cytotoxic agents, and recently developed biological therapeutics. In general, the management of human systemic autoimmune disease is empirical and unsatisfactory. For the most part, broadly immunosuppressive drugs, such as corticosteroids, are used in a wide variety of severe autoimmune and inflammatory disorders. In addition to corticosteroids, other immunosuppressive agents are used in management of the systemic autoimmune diseases. Cyclophosphamide is an alkylating agent that causes profound depletion of both T- and B-lymphocytes and impairment of cell-mediated immunity. Cyclosporine, tacrolimus, and mycophenolate mofetil are natural products with specific properties of T-lymphocyte suppression, and they have been used to treat systemic lupus erythematosus (SLE), rheumatoid arthritis (RA) and, to a limited extent, vasculitis and myositis. These drugs are associated with significant renal toxicity. Methotrexate is also used as a "second line"

agent in RA, with the goal of reducing disease progression. It is also used in polymyositis and other connective-tissue diseases. Other approaches that have been tried include monoclonal antibodies intended to block the action of cytokines or to deplete lymphocytes (Fox, Am J Med 99:82-88, 1995). Treatments for multiple sclerosis (MS) include interferon and copolymer 1, which reduce relapse rate by 20-30% and only have a modest impact on disease progression. MS is also treated with immunosuppressive agents including methylprednisolone, other steroids, methotrexate, cladribine and cyclophosphamide. These immunosuppressive agents have minimal efficacy in treating MS. The introduction of the antibody Tysabri (natalizumab), an alpha 4-integrin antagonist, as treatment for MS has been overshadowed by incidences of progressive multifocal leucoencaphalopathy (PML) in patients receiving the therapy. Current therapy for RA utilizes agents that non-specifically suppress or modulate immune function such as methotrexate, sulfasalazine, hydroxychloroquine, leuflonamide, prednisone, as well as the recently developed TNFα antagonists etanercept and infliximab (Moreland et al., J Rheumatol 28: 1431-52, 2001). Etanercept and infliximab globally block TNFα, making patients more susceptible to death from sepsis, aggravation of chronic mycobacterial infections, and development of demyelinating events.

In the case of organ-specific autoimmunity, a number of different therapeutic approaches have been tried. Soluble protein antigens have been administered systemically to inhibit the subsequent immune response to that antigen. Such therapies include delivery of myelin basic protein, its dominant peptide, or a mixture of myelin proteins to animals with experimental autoimmune encephalomyelitis and humans with multiple sclerosis (Brocke et al., Nature 379: 343-6, 1996; Critchfield et al., Science 263: 1139-43, 1994; Weiner et al., Annu Rev Immunol 12: 809-37, 1994), administration of type II collagen or a mixture of collagen proteins to animals with collagen-induced arthritis and humans with rheumatoid arthritis (Gumanovskaya et al., Immunology 91: 466-73, 1999; McKown et al., Arthritis Rheum 42: 1204-8, 1999; Trentham et al., Science 261: 1727-30, 1993), delivery of insulin to animals and humans with autoimmune diabetes (Pozzilli and Gisella Cavallo, Diabetes Metab Res Rev 16: 306-7, 2000), and delivery of S-antigen to animals and humans with autoimmune uveitis (Nussenblatt et al., Am J Ophthalmol 123: 583-92, 1997). Another approach is the attempt to design rational therapeutic strategies for the systemic administration of a peptide antigen based on the specific interaction between the T-cell receptors and peptides bound to MHC molecules. One study using the peptide approach in an animal model of diabetes resulted in the development of antibody production to the peptide (Hurtenbach et al., J Exp Med 177:1499, 1993). Another approach is the administration of T cell receptor (TCR) peptide immunization (see e.g. Vandenbark et al., Nature 341:541, 1989). Still another approach is the induction of oral tolerance by ingestion of peptide or protein antigens (see e.g. Weiner, Immmunol Today 18:335, 1997).

Mucosal tolerance refers to the phenomenon of systemic tolerance to challenge with an antigen that has previously been administered via a mucosal route, usually oral, nasal or naso-respiratory, but also vaginal and rectal (Weiner et al., Annu Rev Immunol 12:809-837, 1994). Mucosal tolerance was discovered early in the 20th century in models of delayed-type and contact hypersensitivity reactions in guinea pigs, but the mechanisms of tolerance remained ill-defined until the era of modern immunology. The use of cell separation techniques, tests for production of cytokines and transgenic models in which antigen-specific T cells can be tracked in vivo have gradually elucidated mechanisms of mucosal tolerance (Garside and Mowat., Crit Rev Immunol 17:119-137, 1997). It has become evident that antigen administration via mucosal routes can result in distinct types of tolerance, depending on the route of administration and dose of antigen. For example, a high dose of oral antigen induces T-cell activation followed by deletion or anergy of responding T cells (Chen et al., Nature 376:177-180, 1995), analogous to parenteral administration of high-dose soluble antigen. This results in extinction of T cells specific to that antigen and unresponsiveness to subsequent antigen challenge, i.e. passive tolerance. In contrast, a low dose of oral antigen does not induce deletion or anergy but, when given repeatedly, induces a distinct type of immune response characterized by the appearance of regulatory-protective T cells, Treg cells, that secrete anti-inflammatory cytokines, i.e. active tolerance (von Herrath, Res Immunol. 148:541-554, 1997). These Treg cells usually belong to the class of CD4 (helper) T cells. Instillation of intact protein antigen onto the nasopharyngeal mucosa also induces Treg cells that are protective. In this case, both CD4 and CD8 T cells may be induced. Regulatory Treg cells induced after oral or intranasal antigen administration produce anti-inflammatory cytokines such as IL-4, IL-10 and TGF-β. To induce mucosal tolerance, antigen can also be given in the form of aerosol. Administration via these three routes, oral, intranasal and aerosol-inhalation, results in antigen uptake and presentation in different lymphoid compartments in each case. Accordingly, oral antigen is presented to T cells mostly in mesenteric lymph nodes and to some extent in Peyer's patches, intranasal antigen in deep cervical lymph nodes and inhaled antigen in mediastinal lymph nodes. Repeated exposure to antigen in each case is able to induce regulatory T cells, but the nature of these cells differs, depending on the route and form of antigen. While regulatory cells induced by oral antigen are CD4 T cells and express T cell receptors (TCR) consisting of αβ heterodimers, in the case of naso-respiratory antigen, the regulatory cells can also be CD8 T cells expressing a γδ heterodimer TCR (i.e. γδ T cells). Some of these cells may also have a CD8 receptor that is an αα homodimer instead of the conventional αβ-heterodimer TCR. A majority of cells that carry the CD8αα and γδ TCR reside in skin or mucosal tissues.

Over the past decades, there has been a significant increase in both the incidence and prevalence of allergic disease in western countries. Allergic rhinitis is the most common of these diseases, affecting 15-20% of the population. The allergic reaction is triggered by allergen-mediated cross-linking of specific IgE on the surface of mast cells and basophils, leading to release of histamine and other mediators, thus causing an acute allergic reaction, followed by a late-phase reaction characterized by an influx of eosinophils, neutrophils and Th2 cells producing IL-4, IL-5 and IL-13.

Specific immunotherapy (SIT) is recognized as an effective treatment of allergic rhinitis. Traditionally, SIT has been conducted by repeated subcutaneous administration of small amounts of specific allergen. Although this form of treatment can be an effective therapeutic option, concerns exist with the safety of this form of immunotherapy as well as with the difficulty of standardizing the allergen extract used as vaccine. Consequently, there is strong interest in the development of alternative and novel treatments against allergic diseases. One of the approaches is the use of mucosal vaccines (Widermann, Curr Drug Targets Inflamm Allergy 4, 577-583, 2005). Other alternatives are based on the use of allergen derivatives with reduced or no allergenicity as vaccines (Vrtala et al., Methods 32, 313-320, 2004). These include allergens obtained by protein engineering and synthetic peptides representing immunodominant T-cells epitopes of allergens. For example, Ole e1 has been identified as the most relevant allergen of olive pollen (Wheeler et al., Mol Immunol 27, 631-636, 1990).

Immune responses are currently altered by delivering polypeptides, alone or in combination with adjuvants (immunomodulating agents). For example, the hepatitis B virus vaccine contains recombinant hepatitis B virus surface antigen, a non-self antigen, formulated in aluminum hydroxide, which serves as an adjuvant. This vaccine induces an immune response against hepatitis B virus surface antigen to protect against infection. An alternative approach involves delivery of an attenuated, replication deficient, and/or nonpathogenic form of a virus or bacterium, each a non-self antigen, to elicit a host protective immune response against the pathogen. For example, the oral polio vaccine is composed of a live attenuated virus, a non-self antigen, which infects cells and replicates in the vaccinated individual to induce effective immunity against polio virus, a foreign or non-self antigen, without causing clinical disease. Alternatively, the inactivated polio vaccine contains an inactivated or 'killed' virus that is incapable of infecting or replicating and is administered subcutaneously to induce protective immunity against polio virus.

DNA therapies have been described for treatment of autoimmune diseases. Such DNA therapies include DNA molecules encoding the antigen-binding regions of the T cell receptor to alter levels of autoreactive T cells driving the autoimmune response (Waisman et al., Nat Med 2:899-905, 1996; U.S. Pat. No. 5,939,400). DNA molecules encoding autoantigens were attached to particles and delivered by gene gun to the skin to prevent MS and collagen induced arthritis. (WO 97/46253; Ramshaw et al., Immunol Cell Biol 75:409-413, 1997). DNA molecules encoding adhesion molecules, cytokines (e.g., TNFα), chemokines (e.g., C—C chemokines), and other immune molecules (e.g., Fas-ligand) have been used for treatment of autoimmune diseases in animal models (Youssef et al., J Clin Invest 106:361-371, 2000; Wildbaum et al., J Clin Invest 106:671-679, 2000; Wildbaum et al., J Immunol 165:5860-5866, 2000).

Methods for treating autoimmune disease by administering a nucleic acid encoding one or more autoantigens are described in WO 00/53019, WO 2003/045316, and WO 2004/047734. While these methods have been successful, further improvements are still needed.

Bacterial enterotoxins are used as immunostimulating adjuvants in vaccines for the prevention of infectious diseases. Cholera toxin (CT) and the closely related *E. coli* heat-labile toxin (LT) are perhaps the most powerful and best studied mucosal adjuvants in experimental use today (Rappuoli et al., Immunol Today 20:493-500), but when exploited in the clinic, their potential toxicity and association with cases of Bell's palsy (paralysis of the facial nerve) have led to their withdrawal from the market (Gluck et al., J Infect Dis 181: 1129-1132, 2000; Gluck et al., Vaccine 20 (Suppl. 1): S42-44, 2001; Mutsch et al., N Engl J Med. 350: 896-903, 2004). The bacterial enterotoxins CT and LT have proven to be effective immunoenhancers in experimental animals as well as in humans (Freytag et al., Curr Top Microbiol Immunol 236: 215-236, 1999). Structurally, these enterotoxins are $AB_5$ complexes, and consist of one ADP-ribosyltransferase active A1 subunit and an A2 subunit that links the A1 to a pentamer of B subunits. The holotoxins bind to most mammalian cells via the B subunit (CTB), which specifically interacts with the GM1-ganglioside receptor in the cell membrane. Whereas the holotoxins have been found to enhance mucosal immune responses, conjugates between CTB and antigen have been used to specifically tolerize the immune system (Holmgren et al., Am J Trop Med Hyg 50: 42-54, 1994). Studies in mice have shown that CT and LT can accumulate in the olfactory nerve and bulb when given intranasally, a mechanism that is dependent on the ability of the B subunits of CT or LT to bind GM1-ganglioside receptors, present on all nucleated mammalian cells (Fujihashi et al., Vaccine 20: 2431-2438, 2002). Although less toxic mutants of CT and LT have been engineered with substantial adjuvant function, such molecules still carry a significant risk of causing adverse reactions (Giuliani et al., J Exp Med 187: 1123-1132, 1998; Yamamoto et al., J Exp Med 185: 1203-1210, 1997), especially when considering that the adjuvanticity of CT and LT appears to be a combination of the ADP-ribosyltransferase activity of the A subunit and the ability to bind ganglioside receptors on the target cells (Soriani et al., Microbiology 148: 667-676, 2002). These observations and others preclude the use of CT or LT holotoxins in vaccines for humans. On the other hand, recent observations have demonstrated that it is possible to retain adjuvant functions of these molecules with no toxicity or greatly reduced toxicity by introducing site-directed mutations in the gene coding for the A1 subunit. Examples of mutant molecules that have proven to be effective adjuvants are LTK63 and LTR72 (Giuliani et al., J Exp Med 187: 1123-1132, 1998), the former with no enzymatic activity and the latter with significantly reduced ADP-ribosylating ability. Notwithstanding this, the GM1-ganglioside receptor-dependent binding remains a problem in these mutants, and may therefore still cause nerve cell accumulation and neurotoxicity.

A better solution to this dilemma of efficacy versus toxicity is the CTA1-DD molecule that has proven to be a highly effective mucosal and systemic adjuvant (Ågren et al., J Immunol 158: 3936-3946, 1997; U.S. Pat. No. 5,917, 026). This unique adjuvant is based on the enzymatically active A1-subunit of CT, combined with a dimer of an immunoglobulin-binding element from *Staphylococcus aureus* protein A. The molecule thereby avoids binding to all nucleated cells, which could result in unwanted reactions, and exploits fully the CTA1-enzyme in the holotoxin. Accordingly, all studies to date have found that CTA1-DD is nontoxic and has retained excellent immunoenhancing functions. When given systemically, CTA1-DD provides comparable adjuvant effect to that of intact CT, greatly augmenting both cellular and humoral immunity against specific immunogens coadministered with the adjuvant. It also functions as a mucosal adjuvant and should be safe, as it is devoid of the B subunit that is a prerequisite of CT holotoxin toxicity. CTA1-DD cannot bind to ganglioside receptors; rather, it targets B cells, limiting the CTA1-DD adjuvant to a restricted repertoire of cells that it can interact with. However, the adjuvant effect is not completely dependent on B cells, as been shown in strong induction of specific CD4 T cell immunity following intranasal immunizations using the CTA1-DD adjuvant in B-cell deficient mice (Eliasson et al., Vaccine 25: 1243-52, 2008, Akhiani et al., Scand J. Immunol 63: 97-105, 2006).

The adjuvant effect of CTA1-DD was absent in mutants CTA1-E112K-DD and CTA1-R7K-DD, which lack the ADP-ribosylating enzymatic activity (Lycke, Immunol Lett 97: 193-198, 2005).

WO 2009/078796 further describes immunomodulating complexes comprising the mutant CTA1-R7K-DD, and more specifically the immunomodulating complexes comprising CTA1-R7K-DD linked to the shared immunodominant collagen II peptide comprising amino acids 260-273 (CII260-273).

A conjugate of CTB and a peptide derived from bovine collagen II has been shown to be able to protect mice from developing collagen induced autoimmune ear disease as well as collagen-induced arthritis (Kim et al., Ann Otol Rhinol Laryngol 110: 646-654, 2001; Tarkowski et al., Arthritis Rheum 42: 1628-34, 1999). However, CTB may not be suited for human use due to its GM1-ganglioside-binding properties and potential neurotoxic effects, as discussed above.

The immunomodulating complexes of the present invention differ from the immounomodulating complexes comprising the mutant CTA1-R7K-DD according to WO 2009/078796 at least in that amino acid 187 has been changed from cysteine to alanine and, optionally, in that a lysine residue has further been inserted in the N-terminal of the mutant CTA1 subunit.

The inventors of the present invention have surprisingly found that further replacement of amino acid 187 cysteine by an alanine of the immunomodulating complexes comprising the mutant CTA1-R7K-DD according to WO 2009/078796, and in particular the immunomodulating complexes comprising CTA1-R7K-DD linked to the shared immunodominant collagen II peptide, provides a significantly improved therapeutic effect on arthritis, with significantly lower incidence and severity of arthritis in mice.

Without being bound by theory, the mechanism behind the surprising improvement in therapeutic effect of the CTA1-R7K/C187A-DD according to the present invention as compared to CTA1-R/K-DD according to WO 2009/078796 would seem explainable by the fact that the replacement of amino acid 187 cysteine by alanine abolishes the formation of dimers through disulfide bonds.

It was a priori unknown whether obtaining a therapeutic effect would be dependent on at least some or even a substantial degree of dimerisation of the resulting fusion-protein. Therefore, before the surprising findings of the present inventors, it was not predictable whether trying to avoid dimerisation would in fact be detrimental to therapeutic activity of the immunomodulating complexes, and whether making this amino acid replacement would result in a fusion-protein having at least as good therapeutic effects as the CTA1-R7K-DD construct.

Furthermore, the present inventors have surprisingly found that the insertion of a lysine residue in the N-terminal of the fusion protein drastically increases the expression and production of the fusion protein, K-CTA1-R7K/C187A-DD, without any loss with regard to the therapeutic efficacy of the protein due to misfolding, translocation or proteolytic degradation. Thus, it was hitherto unknown whether the insertion of a lysine residue in the N-terminal would be detrimental to the biological availability and therapeutic activity of the fusion protein (e.g. due to effects on folding, etc.), and whether the insertion of lysine in the N-terminal would result in a fusion protein with at least as good therapeutic effects as the CTA1-R7K-DD construct.

BRIEF DESCRIPTION OF THE INVENTION

The present invention relates to improved immunomodulating complexes and compositions comprising them, as well as uses thereof for the production of medicinal products and in methods for the prophylaxis, prevention and/or treatment of autoimmune or allergic diseases. The improved immunomodulating complexes according to the invention are fusion proteins comprising a mutant subunit of the ADP-ribosylating A1-subunit of the cholera toxin (CTA1), a peptide capable of binding to a specific cellular receptor, and one or more epitopes associated with the disease. Administration of a therapeutically or prophylactically effective amount of the immunomodulating complex to a subject elicits suppression of an immune response against an antigen associated with the disease, thereby treating or preventing the disease.

The epitope can be an autoimmune epitope when the disease to be treated is an autoimmune disease and an allergy-provoking epitope when the disease to be treated is an allergic disease.

In one embodiment, the invention provides an immunomodulating complex being a fusion protein comprising:
(a) a mutant subunit of the ADP-ribosylating A1-subunit of the cholera toxin (CTA1),
(b) a peptide capable of binding to a specific cellular receptor, and
(c) one or more epitopes associated with an autoimmune or allergic disease
wherein, in the mutant CTA1 subunit, the amino acids corresponding to the amino acid 7, arginine, and amino acid 187, cysteine, in the native CTA1 have been replaced.

In one preferred embodiment, the amino acid lysine has further been inserted in the N-terminal of the mutant CTA1 subunit.

In one preferred embodiment, the fusion protein comprises the CTA1-R7K/C187A mutant (SEQ ID NO:1), where amino acid 7, arginine, in the native CTA1 sequence has been replaced by a lysine, and where the amino acid 187 cysteine, in the native CTA1 sequence has been replaced by an alanine.

In one even more preferred embodiment, the fusion protein comprises the K-CTA1-R7K/C187A mutant (SEQ ID NO:2), where amino acid 7, arginine, in the native CTA1 sequence has been replaced by a lysine, where the amino acid 187 cysteine, in the native CTA1 sequence has been replaced by an alanine, and the amino acid lysine has been inserted in the N-terminal.

Replacement of amino acid 7, arginine, by a lysine abolishes the ADP-ribosylating activity, replacement of amino acid 187, cysteine, by an alanine prevents the formation of dimers, and the insertion of a lysine in the N-terminal drastically increases the expression and production of fusion protein.

Thus, the fusion protein according to the present invention, K-CTA1-R7K/C187A, provides a surprising and advantageous effect as compared to CTA1-R7K according to WO 2009/078796, which is hereby incorporated in its entirety by reference. Hence, the therapeutic effect of K-CTA1-R7K/C187A-COL-DD has surprisingly been found to be significantly better than the therapeutic effect of CTA1-R7K-COL-DD, as can be seen in the decrease of the severity and incidence of arthritis as compared with the control group of mice in the comparative trials of examples 2 and 3.

In one embodiment, the fusion protein comprises a peptide that specifically binds to a receptor expressed on a cell capable of antigen presentation, especially cells expressing MHC class I or MHC class II antigen. The antigen-presenting cell may be selected from the group consisting of lymphocytes, such as B-lymphocytes, T-cells, monocytes, macrophages, dendritic cells, Langerhans cells, epithelial cells and endothelial cells.

The peptide is a peptide that binds to receptors of the above cells, preferably to an Ig or Fc receptor expressed by said antigen-presenting cell and most preferably to receptors of B-lymphocytes and dendritic cells.

Examples of specific peptides are peptides capable of binding to receptors such as:

(i) granulocyte-macrophage colony-stimulating factor (GM-C SF), capable of binding to the GM-CSF receptor α/β heterodimer present on monocytes, neutrophils, eosinophils, fibroblasts and endothelial cells, (ii) CD4 and CD8, expressed on T cells which, together with the T cell receptor (TcR), act as co-receptors for MHC class II and MHC class I molecules, respectively. MHC class I are expressed on most nucleated cells, whereas MHC class II molecules are expressed on dendritic cells, B cells, monocytes, macrophages, myeloid and erythroid precursor cells and some epithelial cells, (iii) CD 28 and CTLA-4, two homodimeric proteins expressed mainly on T cells which bind to CD80 and CD86B7 expressed on B cells, (iv) CD40, present mainly on the surface of mature B cells which interact with CD40L (gp39 or CD 154) expressed on T cells, (v) different isotypes of the Ig heavy chain constant regions which interact with a number of high or low affinity Fc receptors present on mast cells, basophils, eosinophils, platelets, dendritic cells, macrophages, NK cells and B cells, (vi) complement receptors (CRs), CR1, CR2 and CR3, expressed on B-cells and follicular dendritic cells have been shown to be important in the generation of normal humoral immune responses, and they likely also participate in the development of autoimmunity, (vii) C-type lectin receptors (CLRs), like the Dectin-1 expressed on dendritic cells, (viii) DEC205, an endocytic receptor for antigen uptake and processing expressed at high levels on a subset of dendritic cells, (ix) CD11c, a cell surface receptor for numerous soluble factors and proteins (LPS, fibrinogen, iC3b) found primarily on myeloid cells, (x) the mannose receptor, present on dendritic cells, macrophages and other antigen presenting cells, (xi) the specific HSP60 receptor, present on macrophages.

(xii) CD103, an integrin alpha chain expressed by a subset of dendritic cells.

(xii) the 33D1 antigen, present on dendritic cells.

According to a particularly preferred embodiment of the invention, said peptide is constituted by protein A or a fragment thereof in single or multiple copies, such as one or more D subunits thereof. According to another particularly preferred embodiment of the invention, said peptide is constituted by an antibody fragment, such as a single chain antibody fragment, that specifically binds to a receptor expressed on a cell capable of antigen presentation.

The peptide is preferably such that the resulting fusion protein is in possession of water solubility and capability of targeting the fusion protein to a specific cell receptor different from receptors binding to the native toxin, thereby mediating intracellular uptake of at least said subunit.

The autoantigenic epitopes can be associated with an autoimmune disease, such as insulin-dependent diabetes mellitus (IDDM), multiple sclerosis (MS), systemic lupus erythematosus (SLE), rheumatoid arthritis (RA), or Sjögrens syndrome (SS).

In some embodiments, the autoantigenic epitope associated with IDDM is an epitope derived from the group consisting of: preproinsulin; proinsulin, insulin, and insulin B chain; glutamic acid decarboxylase (GAD) −65 and −67; tyrosine phosphatase IA-2; islet-specific glucose-6-phosphatase-related protein (IGRP) and islet cell antigen 69 kD.

In some embodiments, the autoantigenic epitope associated with MS is an epitope derived from the group consisting of myelin basic protein (MBP), proteolipid protein (PLP), myelin-associated oligodendrocyte basic protein (MOBP), myelin oligodendrocyte glycoprotein (MOG), and myelin-associated glycoprotein (MAG).

In some embodiments, the autoantigenic epitope associated with RA is an epitope derived from the group consisting of type I, II, III, IV, V, IX, and XI collagen, GP-39, filaggrin, and fibrin. In one preferred embodiment, the epitope is derived from collagen type II, preferably the epitope is the shared immunodominant collagen II peptide comprising amino acids 260-273 (CII260-273).

The allergic epitopes can be associated with allergic asthma, allergic rhinitis, allergic alveolitis, atopic dermatitis, or food hypersensitivity. In some embodiments, the allergic epitope is an epitope derived from a plant pollen, such as Ole e1 allergen from olive pollen, the Cry jI and Cry jII allergen from the Japanese cedar pollen, the timothy grass pollen nPhl p4, the major birch pollen allergen Bet v1, or the mugwort pollen major allergen Art v1; an animal antigen, such as the cat allergen Fel d1, the dog allergen Can f1, or the dust mite allergens Der f1, Der p1, Der m1, Blo t4; a fungal antigen, such as the *Alternaria* antigen Alt a1, the *Asperigullus* antigen Asp f1, the *Cladosporium* antigens ClA h1 and Cla h2, or the *Penicillum* antigen Pen ch13; or a food allergen, such as the chicken egg white allergens Gal d1, Gal d2, and Gal d3, the peanut allergen Ara h2, the soybean allergen Gly m1, Gly m5 and Gly m6, the fish allergen Gad c1, or the shrimp allergen Pen a1.

In one preferred embodiment, the immunomodulating complex is the fusion protein K-CTA1-R7K/C187A-COL-DD (SEQ ID NO:4), where COL is the shared immunodominant collagen II peptide comprising amino acids 260-273 (CII260-273) (SEQ ID NO:5). In another embodiment, the immunomodulating complex is the fusion protein CTA1-R7K/C187A-COL-DD (SEQ ID NO:10). In another preferred embodiment, the immunomodulating complex is the fusion protein K-CTA1-R7K/C187A-Ro169-DD (SEQ ID NO:11). In yet another preferred embodiment, the immunomodulating complex is the fusion protein K-CTA1-R7K/C187A-Ro211-DD (SEQ ID NO:12). In yet another preferred embodiment, the immunomodulating complex is the fusion protein K-CTA1-R7K/C187A-Ro274-DD (SEQ ID NO:13). In yet another preferred embodiment, the immunomodulating complex is the fusion protein K-CTA1-R7K/C187A-Betv1-DD (SEQ ID NO:17). In yet another preferred embodiment, the immunomodulating complex is the fusion protein K-CTA1-R7K/C187A-Phlp5-DD (SEQ ID NO:18). In yet another preferred embodiment, the immunomodulating complex is the fusion protein K-CTA1-R7K/C187A-Phlp5-DD (SEQ ID NO:19).

The present invention provides methods and compositions for treatment, prophylaxis and/or prevention of an autoimmune disease such as multiple sclerosis, rheumatoid arthritis, insulin-dependent diabetes mellitus, autoimmune uveitis, Behcet's disease, primary biliary cirrhosis, myasthenia gravis, Sjögren's syndrome, pemphigus vulgaris, scleroderma, pernicious anemia, systemic lupus erythematosus (SLE) and Grave's disease comprising administering to a subject an immunomodulating complex according to the invention comprising one or more autoantigenic epitopes associated with the disease.

In certain embodiments, the present invention provides improved methods for the treatment, prophylaxis and/or prevention of the autoimmune disease insulin-dependent diabetes mellitus (IDDM) comprising administering to a subject an immunomodulating complex according to the invention comprising one or more autoantigenic epitopes associated with IDDM. In some embodiments, the autoantigenic epitopes associated with IDDM are epitopes derived from the group consisting of: preproinsulin; proinsulin, insulin, and insulin B chain; glutamic acid decarboxylase (GAD) −65 and −67; tyrosine phosphatase IA-2; islet-specific glucose-6-phosphatase-related protein (IGRP) and islet cell antigen 69 kD.

In other embodiments of the present invention, improved methods are provided for treatment, prophylaxis and/or prevention of multiple sclerosis (MS) comprising administering to a subject an immunomodulating complex according to the invention comprising one or more autoantigenic epitopes associated with MS. In some embodiments, the autoantigenic epitopes are epitopes derived from the group consisting of myelin basic protein (MBP), proteolipid protein (PLP), myelin-associated oligodendrocyte basic protein (MOBP), myelin oligodendrocyte glycoprotein (MOG), and myelin-associated glycoprotein (MAG).

In other embodiments, improved methods for treatment, prophylaxis and/or prevention of rheumatoid arthritis (RA) are provided comprising administering to a subject an immunomodulating complex according to the invention comprising one or more autoantigenic epitopes associated with RA. In some embodiments, the autoantigenic epitopes are epitopes derived from the group consisting of type I, II, III, IV, V, IX, and XI collagen, GP-39, filaggrin, and fibrin. In one preferred embodiment, the epitope is derived from collagen type II, preferably the epitope is the shared immunodominant collagen II peptide comprising amino acids 260-273 (CII260-273).

Multiple immunomodulating complexes comprising different autoantigenic epitopes may be administered as a cocktail, and each individual immunomodulating complex may comprise multiple autoantigenic epitopes. Similarly, multiple immunomodulating complexes comprising different allergic epitopes may be administered as a cocktail, and each individual immunomodulating complex may comprise multiple allergy-provoking epitopes.

In certain variations, the methods and compositions for the treatment, prophylaxis and/or prevention of an autoimmune or allergic disease further comprise the administration of the immunomodulating complex according to the invention in combination with other substances, such as, for example, polynucleotides comprising an immune modulatory sequence, pharmacological agents, adjuvants, cytokines, or vectors encoding cytokines.

Yet another embodiment of the present invention provides a pharmaceutical composition comprising an immunomodulating complex according to the invention. The pharmaceutical composition of the invention can be used for prophylaxis, prevention and/or treatment of an allergic or autoimmune disease. The autoimmune disease can be selected from the group consisting of insulin-dependent diabetes mellitus, multiple sclerosis, rheumatoid arthritis, autoimmune uveitis, primary biliary cirrhosis, myasthenia gravis, Sjögren's syndrome, pemphigus vulgaris, scleroderma, pernicious anemia, systemic lupus erythematosus, and Grave's disease. The allergic disease can be selected from the group consisting of allergic asthma, allergic rhinitis, allergic alveolitis, atopic dermatitis, or food hypersensitivity.

Yet another embodiment of the present invention provides use of an immunomodulating complex according to the invention for the production of a medicinal product for prophylaxis, prevention and/or treatment of an autoimmune or allergic disease. The autoimmune disease can be selected from the group consisting of insulin-dependent diabetes mellitus, multiple sclerosis, rheumatoid arthritis, autoimmune uveitis, primary biliary cirrhosis, myasthenia gravis, Sjogren's syndrome, pemphigus vulgaris, scleroderma, pernicious anemia, systemic lupus erythematosus, and Grave's disease. The allergic disease can be selected from the group consisting of allergic asthma, allergic rhinitis, allergic alveolitis, atopic dermatitis, or food hypersensitivity.

In yet another embodiment, the present invention provides isolated nucleic acid sequences encoding an immunomodulating complex according to the invention. Accordingly, the present invention provides isolated nucleic acid sequences encoding an immunomodulating complex being a fusion protein comprising a mutant subunit of the ADP-ribosylating A1-subunit of the cholera toxin (CTA1), a peptide capable of binding to a specific cellular receptor, and one or more epitopes associated an autoimmune or allergic disease.

In one embodiment, the nucleic acid according to the invention encodes an immunomodulating complex being a fusion protein comprising:

(a) a mutant subunit of the ADP-ribosylating A1-subunit of the cholera toxin (CTA1), (b) a peptide capable of binding to a specific cellular receptor, and (c) one or more epitopes associated with an autoimmune or allergic disease wherein, in the mutant CTA1 subunit, the amino acids corresponding to the amino acid 7, arginine, and amino acid 187, cysteine, in the native CTA1 have been replaced.

In one preferred embodiment, the amino acid lysine has further been inserted in the N-terminal of the mutant CTA1-subunit.

In one preferred embodiment, the nucleic acid according to the invention encodes a fusion protein comprising the CTA1-R7K/C187A mutant (SEQ ID NO:1), where amino acid 7, arginine, in the native CTA1 sequence has been replaced by a lysine, and where amino acid 187, cysteine, in the native CTA1 sequence has been replaced by an alanine.

In one even more preferred embodiment, the nucleic acid according to the invention encodes a fusion protein comprising the K-CTA1-R7K/C187A mutant (SEQ ID NO:2), where amino acid 7, arginine, in the native CTA1 sequence has been replaced by a lysine, where amino acid 187, cysteine, in the native CTA1 sequence has been replaced by an alanine, and where the amino acid lysine has been inserted in the N-terminal.

In one embodiment, the nucleic acid according to the invention encodes a fusion protein comprising a peptide which specifically binds to a receptor expressed on a cell capable of antigen presentation, especially cells expressing MHC class I or MHC class II molecules. The antigen-presenting cell may be selected from the group consisting of lymphocytes, such as B-lymphocytes, T-cells, monocytes, macrophages, dendritic cells, Langerhans cells, epithelial cells and endothelial cells.

In one embodiment, the nucleic acid according to the invention encodes a fusion protein comprising an autoantigenic epitope associated with an autoimmune disease, such as insulin-dependent diabetes mellitus (IDDM), multiple sclerosis (MS), systemic lupus erythematosus (SLE), rheumatoid arthritis (RA), or Sjögrens syndrome (SS).

In another embodiment, the nucleic acid according to the invention encodes a fusion protein comprising an allergic epitope associated with an allergic disease, such as allergic asthma, allergic rhinitis, allergic alveolitis, atopic dermatitis, or food hypersensitivity.

In some embodiments, the autoantigenic epitope associated with IDDM is an epitope derived from the group consisting of: preproinsulin; proinsulin, insulin, and insulin B chain; glutamic acid decarboxylase (GAD) −65 and −67; tyrosine phosphatase IA-2; islet-specific glucose-6-phosphatase-related protein (IGRP) and islet cell antigen 69 kD. In some embodiments, the autoantigenic epitope associated with MS is an epitope derived from the group consisting of myelin basic protein (MBP), proteolipid protein (PLP), myelin-associated oligodendrocyte basic protein (MOBP), myelin oligodendrocyte glycoprotein (MOG), and myelin-associated glycoprotein (MAG). In some embodiments, the autoantigenic epitope associated with RA is an epitope derived from the group consisting of type I, II, III, IV, V, IX, and XI collagen, GP-39, filaggrin, and fibrin. In some embodiments, the autoantigenic epitope associated with SS is an epitope derived from the group consisting of heat-shock protein HSP60, fodrin, the Ro (or SSA) and the La (or SSB) ribonucleoproteins.

The nucleic acids of the invention can be DNA or RNA.

The nucleic acid according to the invention can be a nucleic acid sequence encoding the fusion protein K-CTA1-R7K/C187A-COL-DD, such as the nucleic acid sequence SEQ ID NO:3; a nucleic acid sequence encoding the fusion protein CTA1-R7K/C187A-COL-DD, such as the nucleic acid sequence SEQ ID NO:9; a nucleic acid sequence encoding the fusion protein K-CTA1-R7K/C187A-Ro169-DD; a nucleic acid sequence encoding the fusion protein K-CTA1-R7K/C187A-Ro211-DD; a nucleic acid sequence encoding the fusion protein K-CTA1-R7K/C187A-Ro274-DD; a nucleic acid sequence encoding the fusion protein K-CTA1-R7K/C187A-Betv1-DD; a nucleic acid sequence encoding the fusion protein K-CTA1-R7K/C187A-Phl p1-DD; and a nucleic acid sequence encoding the fusion protein K-CTA1-R7K/C187A-Phl p5-DD.

In another embodiment, the invention provides a pharmaceutical composition comprising a nucleic acid according to the invention. The pharmaceutical composition can be used for prophylaxis, prevention and/or treatment of an allergic or autoimmune disease. The invention further provides methods for prophylaxis, prevention and/or treatment of an autoimmune or allergic disease in a subject, the method comprising: administering to the subject an effective amount of a nucleic acid according to the invention.

In yet another embodiment, the present invention provides recombinant plasmids, vectors and expression systems comprising a nucleic acid according to the invention. The recombinant expression systems are preferably adapted for bacterial expression. The invention further provides transformed cells containing a plasmid, vector or an expression system according to the invention. The transformed cells are preferably transformed bacterial cells.

DEFINITIONS

Unless defined otherwise, all technical and scientific terms used herein have the same meaning as commonly understood by those of ordinary skill in the art to which this invention belongs. As used herein, the following terms and phrases have the meanings ascribed to them unless specified otherwise.

The amino acid sequence of the ADP-ribosylating A1-subunit of the cholera toxin (CTA1) can be found e.g. in GenBank Accesion Nos. AAM22586.1, ADG44926.1, AAM74170.1, CAE11218.1, or AAA27514.1. The term "a subunit of the ADP-ribosylating A1-subunit of the cholera toxin (CTA1)" refers to a polypeptide comprising at least a sequence corresponding to the sequence from amino acid 7, lysine, to amino acid 187, cysteine, of the sequence of the mature ADP-ribosylating A1-subunit of the cholera toxin (CTA1), such as a polypeptide comprising at least a sequence corresponding to the sequence from amino acid 1, aspargine, to amino acid 187, cysteine, of the sequence of the mature ADP-ribosylating A1-subunit of the cholera toxin (CTA1), or at least a sequence corresponding to the sequence from amino acid 1, aspargine, to amino acid 194, serine, of the sequence of the mature ADP-ribosylating A1-subunit of the cholera toxin (CTA1).

The terms "polynucleotide" and "nucleic acid" refer to a polymer composed of a multiplicity of nucleotide units (ribonucleotide or deoxyribonucleotide or related structural variants) linked via phosphodiester bonds. A polynucleotide or nucleic acid can be of substantially any length, typically from about six (6) nucleotides to about $10^9$ nucleotides or larger. Polynucleotides and nucleic acids include RNA, DNA, synthetic forms, and mixed polymers, both sense and antisense strands, double- or single-stranded, and can also be chemically or biochemically modified or can contain non-natural or derivatized nucleotide bases, as will be readily appreciated by the skilled artisan.

"Antigen," as used herein, refers to any molecule that can be recognized by the immune system that is by B cells or T cells, or both.

"Autoantigen," as used herein, refers to an endogenous molecule, typically a polysaccharide or a protein or fragment thereof, that elicits a pathogenic immune response. Autoantigen includes glycosylated proteins and peptides as well as proteins and peptides carrying other forms of post-translational modifications, including citrullinated peptides. When referring to the autoantigen or epitope thereof as "associated with an autoimmune disease," it is understood to mean that the autoantigen or epitope is involved in the pathophysiology of the disease either by inducing the pathophysiology (i.e., associated with the etiology of the disease), mediating or facilitating a pathophysiologic process; and/or by being the target of a pathophysiologic process. For example, in autoimmune disease, the immune system aberrantly targets autoantigens, causing damage and dysfunction of cells and tissues in which the autoantigen is expressed and/or present. Under normal physiological conditions, autoantigens are ignored by the host immune system through the elimination, inactivation, or lack of activation of immune cells that have the capacity to recognize the autoantigen through a process designated "immune tolerance."

"Allergen" as used herein, refers to an exogenous molecule, typically a polysaccharide or a protein or fragment thereof, that elicits a pathogenic immune response. Allergen includes glycosylated proteins and peptides as well as proteins and peptides carrying other forms of post-translational modifications. The allergen may be derived from e.g. pollen, fungi, insect venom, dander, mold, foodstuffs. Numerous food allergens are purified and well-characterized, such as peanut Ara h1, Ara h2, Ara h3 and Ara h6; chicken egg white Gal d1, Gal d2, and Gal d3; soybean Gly m1; fish-Gad c1; and shrimp-Pen a1. The major cat (Fel d1) and dog (Can f1) allergens, as well as the dust mite allergens Der f1 and Der p1 are well characterized. The native timothy grass pollen nPhl p4 as well as a number of related recombinant allergens, rPhl 1p, rPhl 2p, rPhl 5p, rPhl 6p, rPhl 7p, rPhl 11p, rPhl 12p, the major birch pollen allergen Bet v1, the major plantain pollen allergen Pla I 1, the major olive pollen allergen Ole e1, the major raggweed pollen allergen Amb a1, the major artemesia pollen allergens Art v1 and Art v3, are well defined.

As used herein the term "epitope" is understood to mean a portion of a polysaccharide or polypeptide having a particular shape or structure that is recognized by either B-cells or T-cells of the animal's immune system. An epitope can include portions of both a polysaccharide and a polypeptide, e.g. a glycosylated peptide.

"Autoantigenic epitope" refers to an epitope of an autoantigen that elicits a pathogenic immune response.

"Allergy-provoking epitope" refers to an epitope of an allergen that elicits a pathogenic immune response.

The terms "polypeptide", "peptide", and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

"Self-protein", "self-polypeptide", or self-peptide" are used herein interchangeably and refer to any protein, polypeptide, or peptide, or fragment or derivative thereof that: is encoded within the genome of the animal; is produced or generated in the animal; may be modified posttranslationally at some time during the life of the animal; and, is present in the animal non-physiologically. The term "non-physiological" or "non-physiologically" when used to describe the self-protein(s), -polypeptide(s), or -peptide(s) of this invention means a departure or deviation from the normal role or process in the animal for that self-protein, -polypeptide, or -peptide. When referring to the self-protein, -polypeptide or -peptide as "associated with a disease" or "involved in a disease" it is understood to mean that the self-protein, -polypeptide, or -peptide may be modified in form or structure and thus be unable to perform its physiological role or process or may be involved in the pathophysiology of the condition or disease either by inducing the pathophysiology; mediating or facilitating a pathophysiologic process; and/or by being the target of a pathophysiologic process. For example, in autoimmune disease, the immune system aberrantly attacks self-proteins causing damage and dysfunction of cells and tissues in which the self-protein is expressed and/or present. Alternatively, the self-protein, -polypeptide or -peptide can itself be expressed at non-physiological levels and/or function non-physiologically. For example, in neurodegenerative diseases, self-proteins are aberrantly expressed, and aggregate in lesions in the brain, thereby causing neural dysfunction. In other cases, the self-protein aggravates an undesired condition or process. For example, in osteoarthritis, self-proteins including collagenases and matrix metalloproteinases aberrantly degrade cartilage covering the articular surface of joints. Examples of posttranslational modifications of self-protein(s), -polypeptide(s) or -peptide(s) are glycosylation, addition of lipid groups, reversible phosphorylation, addition of dimethylarginine residues, citrullination, and proteolysis, and more specifically citrullination of fillagrin and fibrin by peptidyl arginine deiminase (PAD), alpha beta-crystallin phosphorylation, citrullination of MBP, and SLE autoantigen proteolysis by caspases and granzymes. Immunologically, self-protein, -polypeptide or -peptide would all be considered host self-antigens and under normal physiological conditions are ignored by the host immune system through the elimination, inactivation, or lack of activation of immune cells that have the capacity to recognize self-antigens through a process designated "immune tolerance". A self-protein, -polypeptide, or -peptide does not include immune proteins, polypeptides, or peptides, which are molecules expressed physiologically exclusively by cells of the immune system for the purpose of regulating immune function. The immune system is the defence mechanism that provides the means to make rapid, highly specific, and protective responses against the myriad of potentially pathogenic microorganisms inhabiting the animal's world. Examples of immune protein(s), polypeptide(s) or peptide(s) are proteins comprising the T-cell receptor, immunoglobulins, cytokines, including the type I interleukins, and the type II cytokines, including the interferons and IL-10, TNF, lymphotoxin, and the chemokines, such as macrophage inflammatory protein −1 alpha and beta, monocyte-chemotactic protein and RANTES, and other molecules directly involved in immune function, such as Fas-ligand. There are certain immune protein(s), polypeptide(s) or peptide(s) that are included in the self-protein, -polypeptide or -peptide of the invention and they are: class I MHC membrane glycoproteins, class II MHC glycoproteins and osteopontin. Self-protein, -polypeptide or -peptide does not include proteins, polypeptides, and peptides that are absent from the subject, either entirely or substantially, due to a genetic or acquired deficiency causing a metabolic or functional disorder, and are replaced either by administration of said protein, polypeptide, or peptide or by administration of a polynucleotide encoding said protein, polypeptide or peptide (gene therapy). Examples of such disorders include Duchenne' muscular dystrophy, Becker's muscular dystrophy, cystic fibrosis, phenylketonuria, galactosemia, maple syrup urine disease, and homocystinuria.

"Modulation of", "modulating", or "altering an immune response" as used herein refers to any alteration of an existing or potential immune responses against an autoimmune or allergy provoking epitope, including, e.g., nucleic acids, lipids, phospholipids, carbohydrates, self-polypeptides, protein complexes, or ribonucleoprotein complexes, that occurs as a result of administration of an immunomodulating complex or polynucleotide encoding an immunomodulating complex. Such modulation includes any alteration in presence, capacity, or function of any immune cell involved in, or capable of being involved in, an immune response. Immune cells include B cells, T cells, NK cells, NK T cells, professional antigen-presenting cells, non-professional antigen-presenting cells, inflammatory cells, or any other cell capable of being involved in or influencing an immune response. "Modulation" includes any change imparted on an existing immune response, a developing immune response, a potential immune response, or the capacity to induce, regulate, influence, or respond to an immune response. Modulation includes any alteration in the expression and/or function of genes, proteins and/or other molecules in immune cells as part of an immune response.

"Modulation of an immune response" includes, for example, the following: elimination, deletion, or sequestration of immune cells; induction or generation of immune cells that can modulate the functional capacity of other cells such as autoreactive lymphocytes, antigen presenting cells, or inflammatory cells; induction of an unresponsive state in immune cells (i.e., anergy); increasing, decreasing, or changing the activity or function of immune cells or the capacity to do so, including, but not limited to, altering the pattern of proteins expressed by these cells. Examples include altered production and/or secretion of certain classes of molecules such as cytokines, chemokines, growth factors, transcription factors, kinases, costimulatory molecules, or other cell surface receptors; or any combination of these modulatory events.

For example, administration of an immunomodulating complex or a polynucleotide encoding an immunomodulating complex can modulate an immune response by eliminating, sequestering, or inactivating immune cells mediating or capable of mediating an undesired immune response; inducing, generating, or turning on immune cells that mediate or are capable of mediating a protective immune response; changing the physical or functional properties of immune cells; or a combination of these effects. Examples of measurements of the modulation of an immune response include, but are not limited to, examination of the presence or absence of immune cell populations (using flow cytometry, immunohistochemistry, histology, electron microscopy, polymerase chain reaction (PCR)); measurement of the functional capacity of immune cells, including ability or resistance to proliferate or divide in response to a signal (such as using T cell proliferation assays and pepscan analysis based on $^3$H-thymidine incorporation following stimulation with anti-CD3 antibody, anti-T cell receptor antibody, anti-CD28 antibody, calcium ionophores, PMA, antigen presenting cells loaded with a peptide or protein antigen; B cell proliferation assays); measurement of the ability to kill or lyse other cells (such as cytotoxic T cell assays); measurements of the cytokines, chemokines, cell surface molecules, antibodies and other products of the cells (e.g., by flow cytometry, enzyme-linked immunosorbent assays, Western blot analysis, protein microarray analysis, immunoprecipitation analysis); measurement of biochemical markers of activation of immune cells or signaling pathways within immune cells (e.g., Western blot and immunoprecipitation analysis of tyrosine, serine or threonine phosphorylation, polypeptide cleavage, and formation or dissociation of protein complexes; protein array analysis; DNA transcriptional, profiling using DNA arrays or subtractive hybridization); measurements of cell death by apoptosis, necrosis, or other mechanisms (e.g., annexin V staining, TUNEL assays, gel electrophoresis to measure DNA laddering, histology; fluorogenic caspase assays, Western blot analysis of caspase substrates); measurement of the genes, proteins, and other molecules produced by immune cells (e.g., Northern blot analysis, polymerase chain reaction, DNA microarrays, protein microarrays, 2-dimentional gel electrophoresis, Western blot analysis, enzyme linked immunosorbent assays, flow cytometry); and measurement of clinical symptoms or outcomes, such as improvement of autoimmune, neurodegenerative, and other diseases involving self proteins or self polypeptides (clinical scores, requirements for use of additional therapies, functional status, imaging studies) for example, by measuring relapse rate or disease severity (using clinical scores known to the ordinarily skilled artisan) in the case of multiple sclerosis, measuring blood glucose in the case of type I diabetes, or joint inflammation in the case of rheumatoid arthritis.

"Subjects" shall mean any animal, such as, for example, a human, non-human primate, horse, cow, dog, cat, mouse, rat, guinea pig or rabbit.

"Treating", "treatment", or "therapy" of a disease or disorder shall mean slowing, stopping or reversing the disease's progression, as evidenced by decreasing, cessation or elimination of either clinical or diagnostic symptoms, by administration of an immunomodulating complex or a polynucleotide encoding an immunomodulating complex, either alone or in combination with another compound as described herein. "Treating", "treatment", or "therapy" also means a decrease in the severity of symptoms in an acute or chronic disease or disorder or a decrease in the relapse rate as, for example, in the case of a relapsing or remitting autoimmune disease course or a decrease in inflammation in the case of an inflammatory aspect of an autoimmune disease. In the preferred embodiment, treating a disease means reversing or stopping or mitigating the disease's progression, ideally to the point of eliminating the disease itself. As used herein, ameliorating a disease and treating a disease are equivalent.

"Preventing", "prophylaxis", or "prevention" of a disease or disorder as used in the context of this invention refers to the administration of an immunomodulating complex or a polynucleotide encoding an immunomodulating complex, either alone or in combination with another compound as described herein, to prevent the occurrence or onset of a disease or disorder or some or all of the symptoms of a disease or disorder or to lessen the likelihood of the onset of a disease or disorder.

A "therapeutically or prophylactically effective amount" of an immunomodulating complex refers to an amount of the immunomodulating complex that is sufficient to treat or prevent the disease as, for example, by ameliorating or eliminating symptoms and/or the cause of the disease. For example, therapeutically effective amounts fall within broad range(s) and are determined through clinical trials, and for a particular patient is determined based upon factors known to the skilled clinician, including, e.g., the severity of the disease, weight of the patient, age, and other factors.

DESCRIPTION OF THE DRAWINGS

FIG. 1. DNA Construct Encoding the Immunomodulating Complex K-CTA1-R7K/C187A-COL-DD The pCTA1-DD plasmid contains the cholera toxin A1 gene (aa 1-194) cloned at HindIII-BamHI and two D fragments from the *staphylococcal* protein A gene under the control of the trp promoter. Collagen peptide was inserted between the CTA1 and the DD fragment to give pCTA1-COL-DD. The R7K and C187A mutations were constructed by in vitro mutagenesis giving p K-CTA1-R7K/C187A-COL-DD. Ptrc=Ptrc promoter. COL2A1=collagen peptide, D=Ig-binding element from *S. aureus* protein A.

FIG. 2. Comparison of the Therapeutic Effects of CTA1-R7K-COL-DD and K-CTA1-R7K/C187A-COL-DD in the Mice CIA Model.

A. Arthritic Index. B. Arthtritis frequency.

-■-CTA1-R7K-COL-DD, -◆-K-CTA1-R7K/C187A-COL-DD, -□-PBS control.

FIG. 3. Comparison of the Therapeutic Effects of CTA1-R7K-COL-DD and K-CTA1-R7K/C187A-COL-DD in the Mice CAIA Model.

Arthritic Index. -■-CTA1-R7K-COL-DD, -◆-K-CTA1-R7K/C187A-COL-DD, -□-PBS control.

FIG. 4. Dimer Formation of CTA1-R7K-COL-DD and K-CTA1-R7K/C187A-COL-DD Studied Using Analytical Size Exclusion Chromatography (SEC).

A. CTA1-R7K-COL-DD, B. K-CTA1-R7K/C187A-COL-DD

FIG. 5. Comparison of Purity of CTA1-R7K-COL-DD and K-CTA1-R7K/C187A-COL-DD by SDS-PAGE.

Lane 1. Molecular weight standard; Lane 2 K-CTA1-R7K/C187A-COL-DD (1.3 μg);

Lane 3 CTA1-R7K-COL-DD (1.1 μg).

DETAILED DESCRIPTION OF THE INVENTION

The present invention relates to improved immunomodulating complexes and compositions comprising them, as well as uses thereof for the production of medicinal products and in methods for the prophylaxis, prevention and/or treatment of a disease in a subject associated with one or more self-protein(s), -polypeptide(s), or -peptide(s) present in the subject and involved in a non-physiological state. The improved immunomodulating complexes according to the invention are fusion proteins comprising a subunit of a mutant A1-subunit of the cholera toxin (CTA1), a peptide capable of binding to a specific cellular receptor, and one or more epitopes associated with the disease. Certain embodiments of the invention are more particularly related to methods and compositions for the prophylaxis, prevention and/or treatment of autoimmune diseases associated with one or more self-polypeptide(s) present in a subject in a non-physiological state such as in multiple sclerosis, rheumatoid arthritis, insulin dependent diabetes mellitus, autoimmune uveitis, primary biliary cirrhosis, myasthenia gravis, Sjögren's syndrome, pemphigus vulgaris, scleroderma, pernicious anemia, systemic lupus erythematosus and Grave's disease. The present invention provides improved methods for the prophylaxis, prevention and/or treatment of an autoimmune disease comprising administering to a subject an immunomodulating complex comprising one or more autoantigenic epitopes associated with the disease. Administration of a therapeutically or prophylactically effective amount of the immunomodulating complex comprising one or more autoantigenic epitopes to a subject elicits suppression of an immune response against an autoantigen associated with the autoimmune disease, thereby treating or preventing the disease.

Autoimmune Diseases

Several examples of autoimmune diseases associated autoantigens are set forth in Table 1, and particular examples are described in further detail herein below.

TABLE 1

Exemplary Autoimmune Diseases and Associated Autoantigens

| Autoimmune Disease | Tissue Targeted | Autoantigen(s) Associated with the Autoimmune Disease |
|---|---|---|
| Rheumatoid Arthritis | synovial joints | immunoglobulin, fibrin, filaggrin, type I, II, III, IV, V, IX, and XI collagens, GP-39, hnRNPs |
| Multiple Sclerosis | central nervous system | myelin basic protein, proteolipid protein, myelin associated glycoprotein, cyclic nucleotide phosphodiesterase, myelin- associated glycoprotein, myelin-associated oligodendrocytic basic protein, myelin oligodendrocyte glycoprotein, alpha-B- crystalin |
| Insulin Dependent Diabetes Mellitus | dependent β cells in islets of pancreas | tyrosine phosphatase IA2, IA-2β; glutamic acid decarboxylase (65 and 67 kDa forms), carboxypeptidase H, insulin, proinsulin, pre-proinsulin, heat shock proteins, glima 38, islet cell antigen 69 KDa, p52, islet cell glucose transporter GLUT-2 |
| Sjögrens Syndrome | exocrine glands | heat shock protein HSP60, fodrin, ribonuceloproteins Ro60 (SSA), Ro52 (SSA), and La (SSB), poly(ADP-ribose) polymerase, lipocalin, alpha amylase |
| Guillian Barre Syndrome | peripheral nervous system | peripheral myelin protein I and others |
| Autoimmune Uveitis | eye, uvea | S-antigen, interphotoreceptor retinoid binding protein (IRBP), rhodopsin, recoverin |
| Primary Biliary Cirrhosis | biliary tree of liver | pyruvate dehydrogenase complexes (2-oxoacid dehydrogenase) |
| Autoimmune Hepatitis | liver | hepatocyte antigens, cytochrome P450 |
| Pemphigus Vulgaris | skin | desmoglein-1, -3, and others |
| Myasthenia Gravis | nerve-muscle junctions | acetylcholine receptor |
| Autoimmune Gastritis | stomach/parietal cell | $H^+/K^+$ ATPase, intrinsic factor |
| Pernicious Anemia | stomach | intrinsic factor |
| Polymyositis | muscle | histidyl tRNA synthetase, other synthetases, other nuclear antigens |
| Autoimmune Thyroiditis | thyroid | thyroglobulin, thyroid peroxidase |
| Graves's Disease | thyroid | thyroid-stimulating hormone receptor |
| Psoriasis | skin | unknown |
| Vitiligo | skin | tyrosinase, tyrosinase-related protein-2 |
| Systemic Lupus Erythematosus | systemic | nuclear antigens: DNA, histones,. ribonucleoproteins |
| Celiac Disease | small bowel | transglutaminase |

Rheumatoid Arthritis.

Rheumatoid arthritis (RA) is a chronic autoimmune inflammatory synovitis affecting 0.8% of the world population. It is characterized by chronic inflammatory synovitis that causes erosive joint destruction. RA is mediated by T cells, B cells and macrophages.

Evidence that T cells play a critical role in RA includes the (1) predominance of $CD4^+$ T cells infiltrating the synovium, (2) clinical improvement associated with suppression of T cell function with drugs such as cyclosporine, and (3) the association of RA with certain HLA-DR alleles. The HLA-DR alleles associated with RA contain a similar sequence of amino acids at positions 67-74 in the third hypervariable region of the 1 chain that are involved in peptide binding and presentation to T cells. RA is mediated by autoreactive T cells that recognize a self-protein, or modified self-protein, present in synovial joints. Autoantigens that are targeted in RA comprise, e.g., epitopes from type II collagen; hnRNP; A2/RA33; Sa; filaggrin; keratin; citrulline; cartilage proteins including gp39; collagens type I5 III, IV, V, IX, XI; HSP-65/60; IgM (rheumatoid factor); RNA polymerase; hnRNP-B1; hnRNP-D; cardiolipin; aldolase A; citrulline-modified filaggrin and fibrin. Autoantibodies that recognize filaggrin peptides containing a modified arginine residue (de-iminated to form citrulline) have been identified in the serum of a high proportion of RA patients. Autoreactive T and B cell responses are both directed against the same immunodominant type II collagen (CII) peptide 257-270 in some patients.

Figure 1:
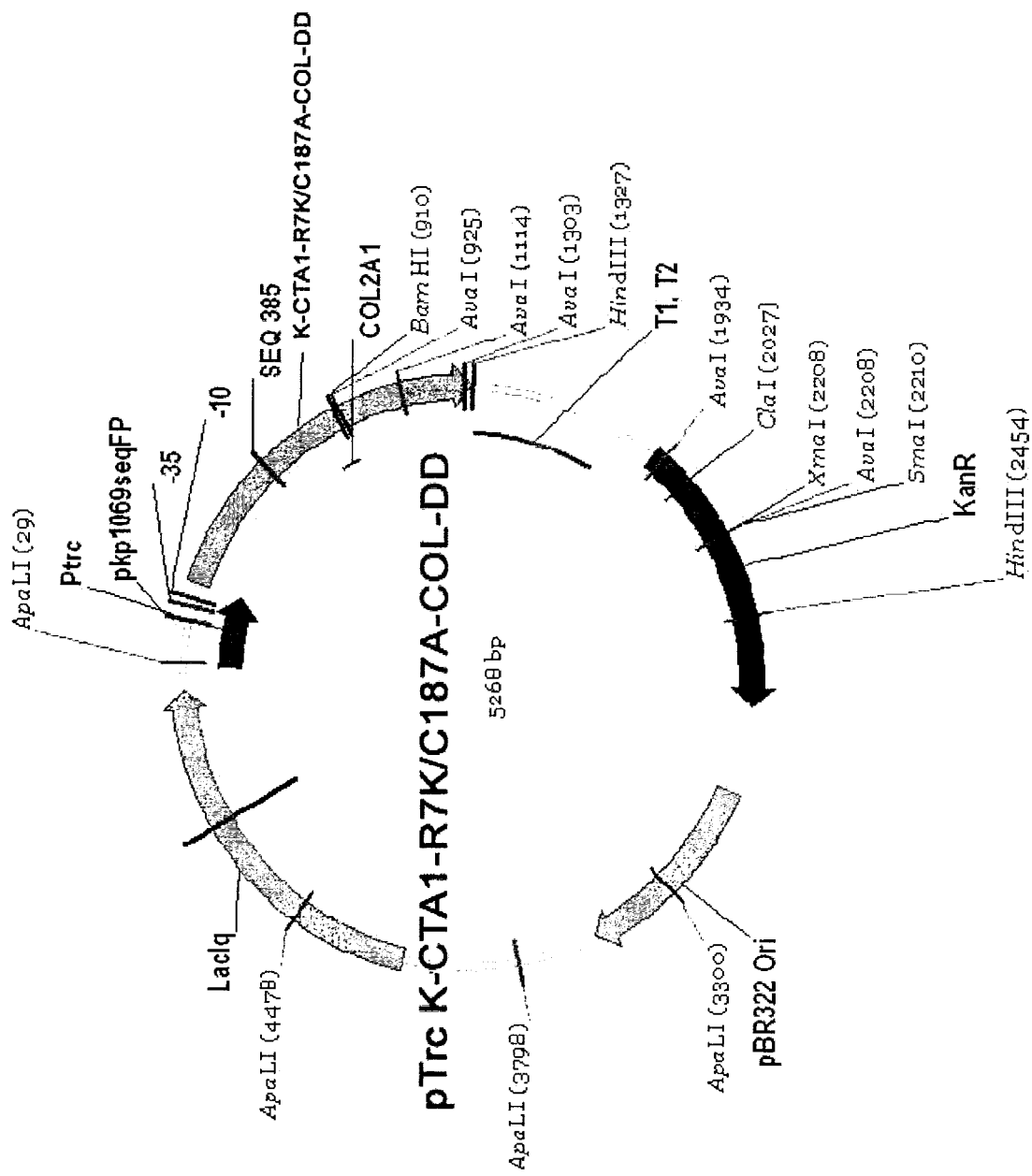

Multiple Sclerosis.

Multiple sclerosis (MS) is the most common demyelinating disorder of the CNS and affects 350,000 Americans and one million people worldwide. Onset of symptoms typically occurs between 20 and 40 years of age and manifests as an acute or sub-acute attack of unilateral visual impairment, muscle weakness, paresthesias, ataxia, vertigo, urinary incontinence, dysarthria, or mental disturbance (in order of decreasing frequency). Such symptoms result from focal lesions of demyelination which cause both negative conduction abnormalities due to slowed axonal conduction, and positive conduction abnormalities due to ectopic impulse generation (e.g., Lhermitte's symptom). Diagnosis of MS is based upon a history including at least two distinct attacks of neurologic dysfunction that are separated in time, produce objective clinical evidence of neurologic dysfunction, and involve separate areas of the CNS white matter. Laboratory studies providing additional objective evidence supporting the diagnosis of MS include magnetic resonance imaging (MRI) of CNS white matter lesions, cerebral spinal fluid (CSF) oligoclonal banding of IgG, and abnormal evoked responses. Although most patients experience a gradually progressive relapsing remitting disease course, the clinical course of MS varies greatly between individuals and can range from being limited to several mild attacks over a lifetime to fulminant chronic progressive disease. A quantitative increase in myelin-autoreactive T cells with the capacity to secrete IFN-gamma is associated with the pathogenesis of MS and EAE.

The autoantigen targets of the autoimmune response in autoimmune demyelinating diseases, such as multiple sclerosis and experimental autoimmune encephalomyelitis (EAE), may comprise epitopes from proteolipid protein (PLP); myelin basic protein (MBP); myelin oligodendrocyte glycoprotein (MOG); cyclic nucleotide phosphodiesterase (CNPase); myelin-associated glycoprotein (MAG) and myelin-associated oligodendrocytic basic protein (MBOP); alpha-B-crystallin (a heat shock protein); viral and bacterial mimicry peptides, e.g., influenza, herpes viruses, hepatitis B virus, etc.; OSP (oligodendrocyte specific-protein); citrulline-modified MBP (the C8 isoform of MBP in which 6 arginines have been de-imminated to citrulline), etc. The integral membrane protein PLP is a dominant autoantigen of myelin. Determinants of PLP antigenicity have been identified in several mouse strains, and include residues 139-151, 103-116, 215-232, 43-64 and 178-191. At least 26 MBP epitopes have been reported (Meinl et al., J Clin Invest 92, 2633-43, 1993). Notable are residues 1-11, 59-76 and 87-99. Immunodominant MOG epitopes that have been identified in several mouse strains include residues 1-22, 35-55, 64-96.

In human MS patients, the following myelin proteins and epitopes were identified as targets of the autoimmune T and B cell response. Antibody eluted from MS brain plaques recognized myelin basic protein (MBP) peptide 83-97 (Wucherpfennig et al., J Clin Invest 100:1114-1122, 1997). Another study found approximately 50% of MS patients having peripheral blood lymphocyte (PBL) T cell reactivity against myelin oligodendrocyte glycoprotein (MOG) (6-10% control). 20% reactive against MBP (8-12% control), 8% reactive against PLP (0% control), 0% reactive against MAG (0% control). In this study, 7 of 10 MOG reactive patients had T cell proliferative responses focused on one of 3 peptide epitopes, including MOG 1-22, MOG 34-56, MOG 64-96 (Kerlero de Rosbo et al., Eur J Immunol 27: 3059-69, 1997). T and B cell (brain lesion-eluted Ab) response focused on MHP 87-99 (Oksenberg et al., Nature 362: 68-70, 1993). In MBP 87-99, the amino acid motif HFFK (SEQ ID NO: 20) is a dominant target of both the T and B cell response (Wucherpfennig et al., J Clin invest 100: 1114-22, 1997). Another study observed lymphocyte reactivity against myelin-associated oligodendrocytic basic protein (MOBP), including residues MOBP 21-39 and MOBP 37-60 (Holz et al., J Immunol 164: 1103-9, 2000). Using immunogold conjugates of MOG and MBP peptides to stain MS and control brains, both MBP and MOG peptides were recognized by MS plaque-bound Abs (Omaha and Hauser, Methods 10: 420-34, 1996).

Insulin Dependent Diabetes Mellitus.

Human type I or insulin-dependent diabetes mellitus (IDDM) is characterized by autoimmune destruction of the p cells in the pancreatic islets of Langerhans. The depletion of 13 cells results in an inability to regulate levels of glucose in the blood. Overt diabetes occurs when the level of glucose in the blood rises above a specific level, usually about 250 mg/dl. In humans, a long presymptomatic period precedes the onset of diabetes. During this period, there is a gradual loss of pancreatic beta cell function. The development of disease is implicated by the presence of autoantibodies against insulin, glutamic acid decarboxylase, and the tyrosine phosphatase IA2 (IA2).

Markers that may be evaluated during the presymptomatic stage are the presence of insulitis in the pancreas, the level and frequency of islet cell antibodies, islet cell surface antibodies, aberrant expression of Class II MHC molecules on pancreatic beta cells, glucose concentration in the blood, and the plasma concentration of insulin. An increase in the number of T lymphocytes in the pancreas, islet cell antibodies and blood glucose is indicative of the disease, as is a decrease in insulin concentration.

The Non-Obese Diabetic (NOD) mouse is an animal model with many clinical, immunological, and histopathological features in common with human IDDM. NOD mice spontaneously develop inflammation of the islets and destruction of the beta cells, which leads to hyperglycemia and overt diabetes. Both CD4$^+$ and CD8$^+$ T cells are required for diabetes to develop, although the roles of each remain unclear. It has been shown that administration of insulin or GADS as proteins, under tolerizing conditions to NOD mice prevents disease and down-regulates responses to the other autoantigens.

The presence of combinations of autoantibodies with various specificities in serum is highly sensitive and specific for human type I diabetes mellitus. For example, the presence of autoantibodies against GAD and/or IA-2 is approximately 98% sensitive and 99% specific for identifying type I diabetes mellitus from control serum. In non-diabetic first degree relatives of type I diabetes patients, the presence of autoantibodies specific for two of the three autoantigens including GAD, insulin and IA-2 conveys a positive predictive value of >90% for development of type IDM within 5 years.

Autoantigens targeted in human insulin dependent diabetes mellitus may include, for example, tyrosine phosphatase IA-2; IA-2[beta]; glutamic acid decarboxylase (GAD) both the 65 kDa and 67 kDa forms; carboxypeptidase H; insulin;

proinsulin; heat shock proteins (HSP); glima 38; islet cell antigen 69 KDa (ICA69); p52; two ganglioside antigens (GT3 and GM2-1); islet-specific glucose-6-phosphatase-related protein (IGRP); and an islet cell glucose transporter (GLUT 2).

Human IDDM is currently treated by monitoring blood glucose levels to guide injection, or pump-based delivery, of recombinant insulin. Diet and exercise regimens contribute to achieving adequate blood glucose control.

Autoimmune Uveitis.

Autoimmune uveitis is an autoimmune disease of the eye that is estimated to affect 400,000 people, with an incidence of 43,000 new cases per year in the U.S. Autoimmune uveitis is currently treated with steroids, immunosuppressive agents such as methotrexate and cyclosporine, intravenous immunoglobulin, and TNFα-antagonists.

Experimental autoimmune uveitis (EAU) is a T cell-mediated autoimmune disease that targets neural retina, uvea, and related tissues in the eye. EAU shares many clinical and immunological features with human autoimmune uveitis, and is induced by peripheral administration of uveitogenic peptide emulsified in Complete Freund's Adjuvant (CFA).

Autoantigens targeted by the autoimmune response in human autoimmune uveitis may include S-antigen, inter-photoreceptor retinoid binding protein (IRBP), rhodopsin, and recoverin.

Primary Billiary Cirrhosis.

Primary Biliary Cirrhosis (PBC) is an organ-specific autoimmune disease that predominantly affects women between 40-60 years of age. The prevalence reported among this group approaches 1 per 1,000. PBC is characterized by progressive destruction of intrahepatic biliary epithelial cells (IBEC) lining the small intrahepatic bile ducts. This leads to obstruction and interference with bile secretion, causing eventual cirrhosis. Association with other autoimmune diseases characterized by epithelium lining/secretory system damage has been reported, including Sjögren's Syndrome, CREST Syndrome, Autoimmune Thyroid Disease and Rheumatoid Arthritis. Attention regarding the driving antigen(s) has focused on the mitochondria for over 50 years, leading to the discovery of the antimitochondrial antibody (AMA) (Gershwin et al., Immunol Rev 174:210-225, 2000; Mackay et al., Immunol Rev 174:226-237, 2000). AMA soon became a cornerstone for laboratory diagnosis of PBC, present in serum of 90-95% patients long before clinical symptoms appear. Autoantigenic reactivities in the mitochondria were designated as M1 and M2. M2 reactivity is directed against a family of components of 48-74 kDa. M2 represents multiple autoantigenic subunits of enzymes of the 2-oxoacid dehydrogenase complex (2-OADC) and is another example of the self-protein, -polypeptide, or -peptide of the instant invention. Studies identifying the role of pyruvate dehydrogenase complex (PDC) antigens in the etiopathogenesis of PBC support the concept that PDC plays a central role in the induction of the disease (Gershwin et al., Immunol Rev 174:210-225, 2000; Mackay et al., Immunol Rev 174:226-237, 2000). The most frequent reactivity in 95% of cases of PBC is the E2 74 kDa subunit, belonging to the PDC-E2. There exist related but distinct complexes including: 2-oxoglutarate dehydrogenase complex (OGDC) and branched-chain (BC) 2-OADC. Three constituent enzymes (E1,2,3) contribute to the catalytic function, which is to transform the 2-oxoacid substrate to acyl co-enzyme A (CoA), with reduction of NAD to NADH. Mammalian PDC contains an additional component, termed protein X or E-3 Binding protein: (E3BP). In PBC patients, the major antigenic response is directed against PDC-E2 and E3BP. The E2 polypeptide contains two tandemly repeated lipoyl domains, while E3BP has a single lipoyl domain. The lipoyl domain is found in a number of autoantigen targets of PBC and is referred to herein as the "PBC lipoyl domain." PBC is treated with glucocorticoids and immunosuppressive agents, including methotrexate and cyclosporin A.

Sjögren's Syndrome.

Sjögren's syndrome (SS) is a chronic autoimmune disease that affects primarily salivary and lacrimal glands, leading to dry eyes (keratoconjunctivitis sicca) and dry mouth (xerostomia). Other organs that may be involved include the bronchial tree, kidneys, liver, blood vessels, peripheral nerves and the pancreas. Of particular interest is the dual presentation of SS: either alone as a primary disorder in women of the fourth and fifth decades (primary SS), or in the context of other autoimmune diseases (secondary SS); glandular (sicca symptoms) and systemic (extraglandular) clinical manifestations may be present. Characteristic of SS is the presence of rheumatoid factors, antinuclear and precipitating autoantibodies. The cytoplasmic/nuclear ribonucleoprotein particles (Ro/SSA and La/SSB) have a prominent role in the autoimmune response of SS. Other antigens involved in the positive nuclear pattern by immunofluorescence include the following: Ku, NOR-90 (nucleolar organizing region), p-80 coilin, HMG-17 (high-mobility group), Ki/SL. Furthermore, organ-specific autoantibodies are also recognized, including antithyroglobulin, antierythrocyte and antisalivary gland epithelium antibodies. (Reviewed in Clio et al., Int Arch Allergy Immunol 123:46-57, 200). A 120-kD organ-specific autoantigen has been identified as the cytoskeletal protein α-fodrin (Haneji et al., Science 276:604-607, 1997). HSP60 is another autoantigen suggested to be involved in SS. Immunization with HSP60 or a HSP60-derived peptide (amino acid residues 437-460) have been shown to reduce SS-related histopathologic features in an animal model of SS (Dalaleu et al., Arthritis Rheum 58:2318-2328, 2008). The major target antigens Ro/SSA, La/SSB and their cognate antibodies have been extensively defined at the molecular level. Ro/SSA is a ribonucleoprotein containing small cytoplasmic RNAs. The protein component of the Ro/SSA antigen, a 60-kD protein (60-kD Ro/SSA, Ro60), is bound to one of several small cytoplasmic RNA molecules. A 52-kD peptide is another component of Ro/SSA antigen (52-kD Ro/SSA; Ro52). La/SSB antigen is composed of a polypeptide consisting of 408 amino acids. Both 60-kD Ro/SSA and La/SSB proteins are members of a family of RNA-binding proteins that contain a sequence of 80 amino acids known as the RNA recognition motif (RNP). B cell epitope mapping of 60-kD Ro/SSA, 52-kD Ro/SSA and La/SSB molecules using several strategies have revealed specific epitopes in several studies. B cell epitopes of 60-kD Ro/SSA autoantigen appear to be located in the central region and the carboxy-terminal part of the molecule. Two disease-specific epitopes: the TKYKQRNGWSHKDLLR-SHLKP (169-190) (SEQ ID NO:6) and the ELYKEKALS-VETEKLLKYLEAV (211-232) (SEQ ID NO:7) region have been identified (Routsias et al., Eur J Clin Invest 26:514-521, 1996). The antigenic determinants of 52-kD Ro/SSA protein are mainly linear and are found in the central part of the molecule. Four peptides (amino acids 2-11, 107-126, 277-292 and 365-382) have been reported to be recognized by anti-Ro/SSA sera (Ricchiuti et al., Clin Exp Immunol 95:397-407, 1994). Four highly reactive peptides with purified IgG, spanning the regions 145-164, 289-308, 301-320 and 349-368 of the La/SSB protein, have been reported (Tzioufas et al., Clin Exp Immunol 108:191-198, 1997).

Other Autoimmune Diseases and Associated Autoantigens.

Autoantigens for myasthenia gravis may include epitopes within the acetylcholine receptor. Autoantigens targeted in pemphigus vulgaris may include desmoglein-3. Panels for myositis may include tRNA synthetases (e.g., threonyl, histidyl, alanyl, isoleucyl, and grycyl); Ku; Scl; SSA; U1 Sn ribonuclear protein; Mi-I; Mi-I; Jo-I; Ku; and SRP. Panels for scleroderma may include Scl-70; centromere; U1 ribonuclear proteins; and fibrillarin. Panels for pernicious anemia may include intrinsic factor; and glycoprotein beta subunit of gastric H/K ATPase. Epitope antigens for systemic lupus erythematosus (SLE) may include DNA; phospholipids; nuclear antigens; Ro; La; U1 ribonucleoprotein; Ro60 (SS-A); Ro52 (SS-A); La (SS-B); calreticulin; Grp78; Scl-70; histone; Sm protein; and chromatin, etc. For Grave's disease, epitopes may include the Na+/I-symporter; thyrotropin receptor; Tg; and TPO.

Graft Versus Host Disease.

One of the greatest limitations of tissue and organ transplantation in humans is rejection of the tissue transplant by the recipient's immune system. It is well established that the greater the matching of the MHC class I and II (HLA-A, HLA-B, and HLA-DR) alleles between donor and recipient the better the graft survival. Graft versus host disease (GVHD) causes significant morbidity and mortality in patients receiving transplants containing allogeneic hematopoietic cells. Hematopoietic cells are present in bone-marrow transplants, stem cell transplants, and other transplants. Approximately 50% of patients receiving a transplant from a HLA-matched sibling will develop moderate to severe GVHD, and the incidence is much higher in non-HLA-matched grafts. One-third of patients that develop moderate to severe GVHD will die as a result. T lymphocytes and other immune cell in the donor graft attack the recipients' cells that express polypeptide variations in their amino acid sequences, particularly variations in proteins encoded in the major histocompatibility complex (MHC) gene complex on chromosome 6 in humans. The most influential proteins for GVHD in transplants involving allogeneic hematopoietic cells are the highly polymorphic (extensive amino acid variation between people) class I proteins (HLA-A, -B, and -C) and the class II proteins (DRB1, DQB1, and DPB1) (Appelbaum, Nature 411, 385-389, 2001). Even when the MHC class I alleles are serologically 'matched' between donor and recipient, DNA sequencing reveals there are allele-level mismatches in 30% of cases providing a basis for class I-directed GVHD even in matched donor-recipient pairs (Appelbaum, Nature 411, 385-389, 2001). The minor histocompatibility self-antigens in GVHD frequently cause damage to the skin, intestine, liver, lung, and pancreas. GVHD is treated with glucocorticoids, cyclosporine, methotrexate, fludarabine, and OKT3.

Tissue Transplant Rejection.

Immune rejection of tissue transplants, including lung, heart, liver, kidney, pancreas, and other organs and tissues, is mediated by immune responses in the transplant recipient directed against the transplanted organ. Allogeneic transplanted organs contain proteins with variations in their amino acid sequences when compared to the amino acid sequences of the transplant recipient. Because the amino acid sequences of the transplanted organ differ from those of the transplant recipient they frequently elicit an immune response in the recipient against the transplanted organ. Rejection of transplanted organs is a major complication and limitation of tissue transplantation, and can cause failure of the transplanted organ in the recipient. The chronic inflammation that results from rejection frequently leads to dysfunction in the transplanted organ. Transplant recipients are currently treated with a variety of immunosuppressive agents to prevent and suppress rejection. These agents include glucocorticoids, cyclosporin A, Cellcept, FK-506, and OKT3.

Compositions and Methods for Treatment

The present invention provides improved immunomodulating complexes and compositions comprising them, as well as uses thereof for the production of medicinal products and in methods for the treatment, prophylaxis and/or prevention of autoimmune or allergic diseases. The improved immunomodulating complexes according to the present invention are fusion proteins comprising a mutant subunit of the ADP-ribosylating A1-subunit of the cholera toxin (CTA1), a peptide capable of binding to a specific receptor, and one or more epitopes associated with the autoimmune or allergic disease. The improved method of the present invention includes the administration of an immunomodulating complex comprising one or more epitopes associated with the disease.

In certain embodiments, the present invention provides improved methods for the treatment, prophylaxis and/or prevention of the autoimmune disease insulin-dependent diabetes mellitus (IDDM) comprising administering to a subject an immunomodulating complex comprising one or more autoantigenic epitopes associated with IDDM.

The immunomodulating complex administered to treat or prevent IDDM may include autoimmune epitopes derived from one or more of self-proteins, for example preproinsulin, proinsulin, glutamic acid decarboxylase (GAD) −65 and −67; tyrosine phosphatase IA-2; islet-specific glucose-6-phosphatase-related protein (IGRP); and/or islet cell antigen 69 kD. Alternatively, the immunomodulating complex administered to treat or prevent IDDM may include multiple autoimmune epitopes derived form the same or different self-protein(s), -polypeptide(s), or -peptide(s). In preferred embodiments, the immunomodulating complex administered to treat or prevent IDDM may include autoimmune epitopes derived the self-polypeptide preproinsulin or proinsulin.

In other embodiments of the present invention, improved methods are provided for the treatment, prophylaxis and/or prevention of multiple sclerosis (MS) comprising administering to a subject an immunomodulating complex comprising one or more autoantigenic epitopes associated with MS. The immunomodulating complex administered to treat MS may include an autoantigen epitope derived from one or more self-polypeptides including, but not limited to: myelin basic protein (MBP), myelin oligodendrocyte glycoprotein (MOG), proteolipid protein (PLP), myelin-associated oligodendrocytic basic protein (MOBP), myelin oligodendrocyte glycoprotein (MOG), and/or myelin-associated glycoprotein (MAG). Alternatively, an immunomodulating complex comprising multiple autoantigenic epitopes derived form the same or different self-protein(s), -polypeptide(s), or -peptide(s) associated with the disease.

In other embodiments of the present invention, improved methods for the treatment, prophylaxis and/or prevention of rheumatoid arthritis (RA) are provided comprising administering to a subject an immunomodulating complex according to the invention comprising one or more autoantigenic epitopes associated with RA. In some embodiments, the autoantigenic epitope is an epitope derived from the group consisting of type I, II, III, IV, V, IX, and XI collagen, GP-39, filaggrin, and fibrin. In one preferred embodiment, the epitope is derived from collagen type II, preferably the epitope is the shared immunodominant collagen II peptide comprising amino acids 260-273 (CII260-273), SEQ ID NO:5.

Alternatively, multiple immunomodulating complexes comprising autoantigenic epitopes derived from different self-polypeptides may be administered.

Thus, the therapeutic effect of the immunomodulating complex according to the present invention, as demonstrated in the examples (particularly in the rheumatoid arthritis models, CIA in example 2 and CAIA in example 3, and indicated in the EAE model), is not specifically limited to rheumatoid arthritis (RA), but is an advantageous therapeutic effect associated with the treatment, prophylaxis and prevention of autoimmune and allergic diseases in general, depending on the choice of epitope from an autoantigen associated with the specific allergic or autoimmune disease. Thus, the examples of the present invention are intended to illustrate and support the general inventive concept of using the immunomodulating complexes according to the invention comprising the immunomodulating CTA1-R7K/C187A in connection with an immunodominant epitope for the treatment of autoimmune and allergic diseases in general.

The shared immunodominant epitope may be selected from any suitable autoantigen known to be associated with an autoimmune or allergic disease. The epitope may, for instance, be selected from any of the autoantigens associated with the diseases in table 1.

However, epitopes with a high content of cysteine may counteract the advantageous effect provided by the replacement of amino acid 187 cysteine by an alanine in CTA1-R7K/C187A of the immunomodulating complex according to the invention as compared to CTA1-R7K. Therefore, it is preferable that epitopes according to the present invention are chosen in such a way as to avoid high contents of cysteine.

In yet another embodiment, the present invention provides nucleic acid sequences, including DNA and RNA sequences, encoding the immunomodulating complexes according to the invention as well as plasmids, vectors and expression systems comprising such nucleic acid sequences.

The immunomodulating complexes according to the invention can be produced by recombinant DNA technology.

Techniques for construction of plasmids, vectors and expression systems and transfection of cells are well-known in the art, and the skilled artisan will be familiar with the standard resource materials that describe specific conditions and procedures.

Construction of the plasmids, vectors and expression system of the invention employs standard ligation and restriction techniques that are well-known in the art (see generally, e.g., Ausubel et al., Current Protocols in Molecular Biology, Wiley Interscience, 1989; Sambrook and Russell, Molecular Cloning, A Laboratory Manual 3rd ed. 2001). Isolated plasmids, DNA sequences, or synthesized oligonucleotides are cleaved, tailored, and religated in the form desired. Sequences of DNA constructs can be confirmed using, e.g., standard methods for DNA sequence analysis (see, e.g., Sanger et al. (1977), Proc. Natl. Acad. Sci., 74, 5463-5467).

Yet another convenient method for isolating specific nucleic acid molecules is by the polymerase chain reaction (PCR) (Mullis et al., *Methods Enzymol* 155:335-350, 1987) or reverse transcription PCR (RT-PCR). Specific nucleic acid sequences can be isolated from RNA by RT-PCR. RNA is isolated from, for example, cells, tissues, or whole organisms by techniques known to one skilled in the art. Complementary DNA (cDNA) is then generated using poly-dT or random hexamer primers, deoxynucleotides, and a suitable reverse transcriptase enzyme. The desired polynucleotide can then be amplified from the generated cDNA by PCR. Alternatively, the polynucleotide of interest can be directly amplified from an appropriate cDNA library. Primers that hybridize with both the 5' and 3' ends of the polynucleotide sequence of interest are synthesized and used for the PCR. The primers may also contain specific restriction enzyme sites at the 5' end for easy digestion and ligation of amplified sequence into a similarly restriction digested plasmid vector.

Delivery of Immunomodulating Complexes

Therapeutically and prophylactically effective amounts of an immunomodulating complex are in the range of about 1 µg to about 10 mg. A preferred therapeutic or prophylactically effective amount of an immunomodulating complex is in the range of about 5 µg to about 1 mg. A most preferred therapeutic amount of immunomodulating complex is in the range of about 10 µg to 100 µg. In certain embodiments, the immunomodulating complex is administered monthly for 6-12 months, and then every 3-12 months as a maintenance dose. Alternative treatment regimens may be developed and may range from daily, to weekly, to every other month, to yearly, to a one-time administration, depending upon the severity of the disease, the age of the patient, the immunomodulating complex being administered, and such other factors as would be considered by the ordinary treating physician.

In one embodiment, the immunomodulating complex is delivered intranasally. In other variations, the immunomodulating complex is delivered orally, sublingually, subcutaneously, transcutaneously, intradermally, intravenously, mucosally or intramuscularly.

Formulation

The immunomodulating complex can be administered in combination with other substances, such as, for example, pharmacological agents, adjuvants, cytokines, or immune stimulating complexes (ISCOMS).

TABLE 2

| Sequences | | |
| --- | --- | --- |
| CTA1-R7K/C187A | Amino acid sequence | SEQ ID NO: 1 |
| K-CTA1-R7K/C187A | Amino acid sequence | SEQ ID NO: 2 |
| K-CTA1-R7K/C187A-COL-DD | DNA sequence | SEQ ID NO: 3 |
| K-CTA1-R7K/C187A-COL-DD | Amino acid sequence | SEQ ID NO: 4 |
| COL, collagen II amino acids 260-273 | Amino acid sequence | SEQ ID NO: 5 |
| 60-kD Ro/SSA amino acids 169-190 | Amino acid sequence | SEQ ID NO: 6 |

TABLE 2-continued

Sequences

| | |
|---|---|
| 60-kD Ro/SSA amino acids 211-232 | Amino acid sequence SEQ ID NO: 7 |
| 60-kD Ro/SSA amino acids 274-290 | Amino acid sequence SEQ ID NO: 8 |
| CTA1-R7K/C187A-COL-DD | DNA sequence SEQ ID NO: 9 |
| CTA1-R7K/C187A-COL-DD | Amino acid sequence SEQ ID NO: 10 |
| K-CTA1-R7K/C187A-Ro169-DD | Amino acid sequence SEQ ID NO: 11 |
| K-CTA1-R7K/C187A-Ro211-DD | Amino acid sequence SEQ ID NO: 12 |
| K-CTA1-R7K/C187A-Ro274-DD | Amino acid sequence SEQ ID NO: 13 |
| Bet v 1 amino acids 140-151 | Amino acid sequence SEQ ID NO: 14 |
| Phl p 1 amino acids 150-164 | Amino acid sequence SEQ ID NO: 15 |
| Phl p 5 amino acids 216-233 | Amino acid sequence SEQ ID NO: 16 |
| K-CTA1-R7K/C187A-Betv1-DD | Amino acid sequence SEQ ID NO: 17 |
| K-CTA1-R7K/C187A-Phl p1-DD | Amino acid sequence SEQ ID NO: 18 |
| K-CTA1-R7K/C187A-Phl p5-DD | Amino acid sequence SEQ ID NO: 19 |

EXAMPLES

The following examples are specific embodiments for carrying out the present invention. The examples are offered for illustrative purposes only, and are not intended to limit the scope of the present invention in any way.

Example 1

Immunomodulating Complex
K-CTA1-R7K/C187A-COL-DD

Construction of CTA1-DD mutants, expression and purification of fusion proteins were performed essentially as described by Ågren (J Immunol 1999, 162: 2432-2440).

The pCTA1-DD plasmid contains the cholera toxin A1 gene (aa 1-194) cloned at HindIII-BamHI and DNA coding two D fragments from the *staphylococcal* protein A gene under the control of the trp promoter. DNA encoding a collagen peptide, the shared immunodominant collagen II peptide (CII260-273), was inserted between DNA encoding the CTA1 and the DD moieties giving the pCTA1-COL-DD plasmid. The R7K and C187A mutations were constructed by in vitro mutagenesis giving the plasmid pK-CTA1-R7K/C187A-COL-DD (FIG. 1).

Example 2

Comparison of the Therapeutic Effects of
CTA1-R7K-COL-DD and
K-CTA1-R7K/C187A-COL-DD in the Mice CIA Model The mouse Collagen Induced Arthritis (CIA) model of RA was used to compare intranasal treatments with the CTA1-R7K-COL-DD and K-CTA1-R7K/C187A-COL-DD tolerogen. The CIA model shares a number of clinical, histologic, and immunologic features with RA, and is therefore the most used model to test potential therapeutic agents against RA. DBA1 mice (Taconic, Denmark) were given a primary immunization with 100 μg chicken/bovine collagen type II (Sigma/MDBioSciences) in complete Freund's adjuvant (CFA) followed by a booster with incomplete Freund's adjuvant (IFA) on day 21. The mice were treated intranasally with 3-8 doses of PBS, CTA1-R7K-COL-DD or K-CTA1-R7K/C187A-COL-DD around the time of and/or after the booster immunization. Mice were then followed with regard to the incidence and severity of arthritis using a scoring system for arthritis.

A clinical scoring system of 0-3 points for each limb was used: 0=no inflammation, 0.5=toe or finger swelling, 1=mild swelling or redness, 2=swelling and redness, and 3=marked swelling, redness and/or ankylosis. The arthritis index was constructed by adding the scores from all four limbs for each animal.

Figure 2:
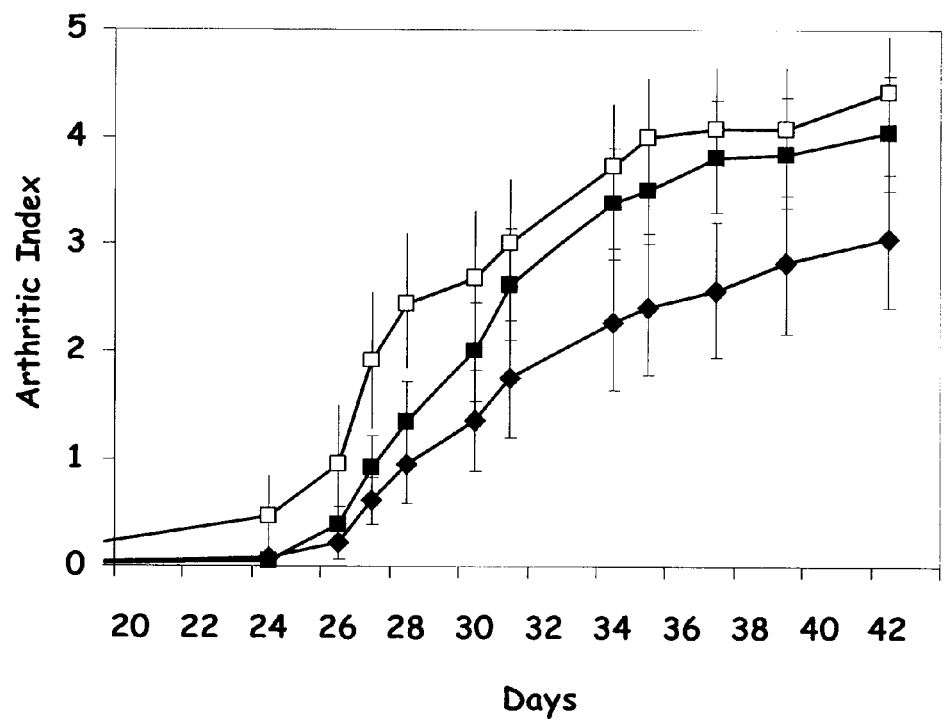
Figure 2:
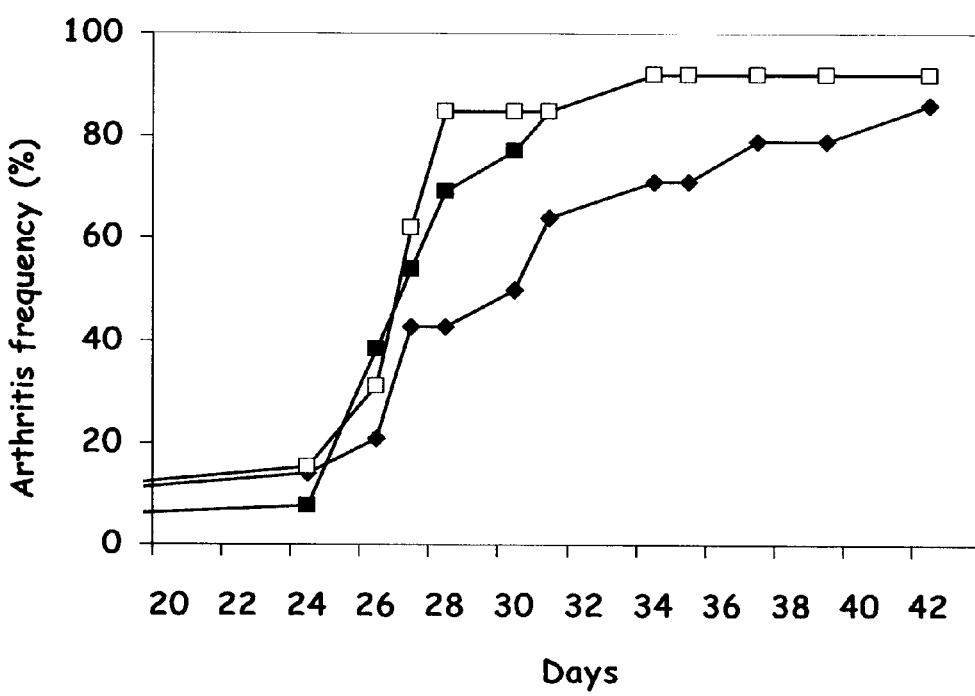
Figure 3:
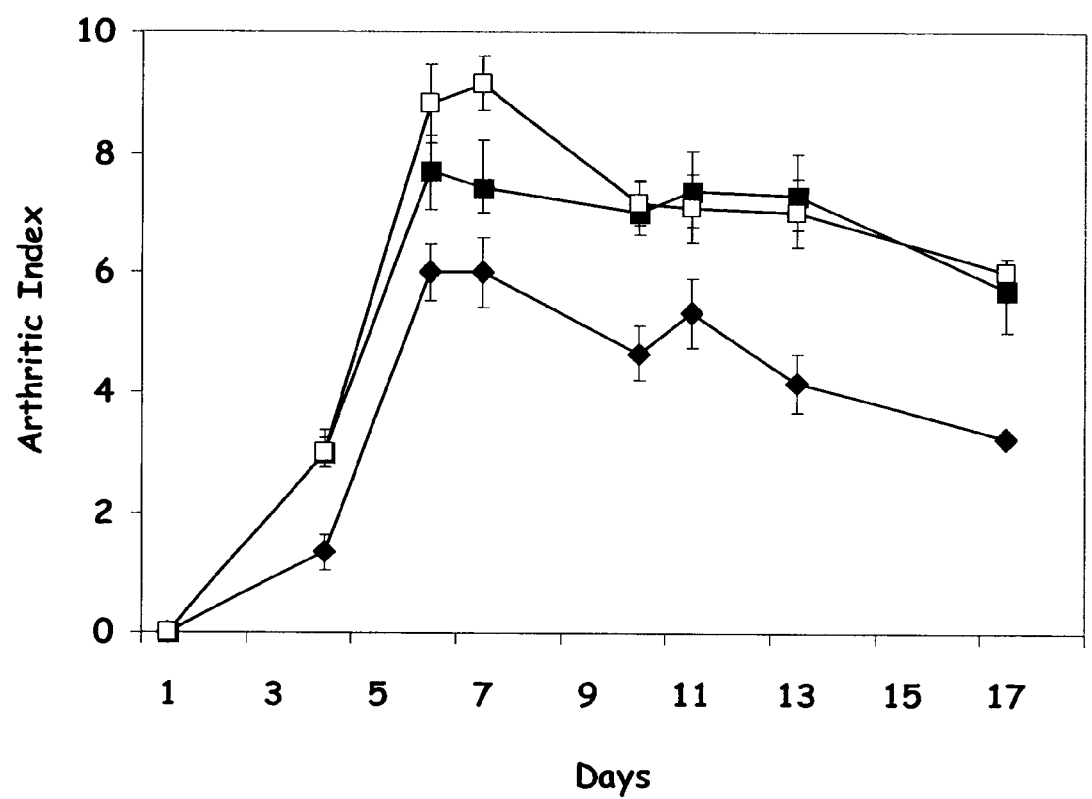

The therapeutic effect of K-CTA1-R7K/C187A-COL-DD was significantly better than the therapeutic effect of CTA1-R7K-COL-DD, as seen in the decrease of the severity (FIG. 2A) and incidence (FIG. 2B) of CIA as compared with the control group (PBS).

The arthritis index in the control PBS group increased dramatically three weeks after the collagen-immunizations and reached a peak at 6 weeks. In the CTA1-R7K-COL-DD group, a slight decrease in arthritis index could be seen. By contrast, in the K-CTA1-R7K/C187A-COL-DD group, the arthritis index was significantly lower, and many animals had no symptoms at all.

Example 3

Comparison of the Therapeutic Effects of
CTA1-R7K-COL-DD and
K-CTA1-R7K/C187A-COL-DD in the Mice CAIA Model Collagen Antibody-Induced Arthritis (CAIA) was induced in Balb/c mice (Taconic, Denmark) day 0 by an intravenous injection of a cocktail of monoclonal antibodies to Collagen II (ArthritoMab cocktail: D1, F10, A2 and D8; MD Biosciences, Zurich, Switzerland) at a dose level of 2 mg/mouse. On day 3, lipopolysaccharide (LPS) (ArthritoMab kit, MD Biosciences) was injected intraperitonally to enhance the incidence and severity of the disease (50 μg/mouse).

The mice were treated intranasally on day −2, 0, +3 with 5 μg K-CTA1-R7K/C187A-COL-DD or CTA1-R7K-COL-DD in 20 μl PBS. The mice were followed with regard to the incidence and severity of arthritis using the same scoring system for arthritis as for CIA (see Example 2).

On day 4, all mice started to show signs of disease (data not shown). In the PBS control group and in the group treated with CTA1-R7K-COL-DD, the arthritic index increased dramatically 7 days after antibody immunization. However, in the group treated with K-CTA1-R7K/C187A-COL-DD the increase in arthritic index was significantly lower throughout the course of the experiment.

Example 4

Immunomodulating Complexes for the Treatment of Sjögrens Disease (SS)

DNA sequences encoding epitopes derived from 60 kDa Ro, Ro169, with the amino acid sequence TKYKQRNGWSHKDLLRSHLKP (SEQ ID NO:6), and Ro 211, with the amino sequence ELYKEKALSVETEKLLKYLEAV (SEQ ID NO:7), and Ro274, with amino acid sequence QEMPLTALLRNLGKMT (SEQ ID NO:8), are cloned into the K-CTA1-R7K/C187A vector, resulting in vectors comprising DNA constructs encoding the immunomodulating complexes K-CTA1-R7K/C187A-Ro169-DD (SEQ ID NO:11), K-CTA1-R7K/C187A-Ro211-DD (SEQ ID NO:12), and K-CTA1-R7K/C187A-Ro274-DD (SEQ ID NO:13), respectively.

Expression vectors are transfected into *E. coli* and the expressed immunomodulating complexes are purified using standard techniques.

Example 5

Therapeutic Effects of Immunomodulating Complexes for the Treatment of Sjögren's Disease (SS)

Recently, a novel murine model that shows striking similarity to many features of the human disease was created (Scofield R. H. et al., J Immunol, 2005, 175 (12), 8409-12), in which BALB/c mice were immunized over a time period with a short peptide of the human Ro RNP (Ro274-290, designated Ro274) having a 100% homology to the mouse sequence. It was determined that the mice immunized with this peptide develop high-titer IgG autoantibodies against Ro52, Ro60 and La, salivary gland infiltration of CD19+ B and CD4+/8+ lymphocytes, and decreased salivary flow. This model is thus suitable for studying the therapeutic effects of immunomodulating complexes for the treatment of Sjögren's disease (SS).

In brief, animals are immunized with a peptide corresponding to amino acids 274-290 of the 60-kDa Ro protein, QEMPLTALLRNLGKMT (SEQ ID NO:8). Immunization is conducted using 100 μg of monomer peptide in PBS emulsified 1:1 in CFA for the initial immunization, with subsequent immunization in IFA on days 14, 35, 63, and 51. Disease is followed by measuring salivary production as follows: Briefly, animals are fasted for 16-18 h before the procedure. An i.p. injection of 2.5% 2,2,2-tribromoethanol at 0.01 ml/g body weight is given to each animal as anesthesia. Saliva secretion is then stimulated with an i.p. injection of 0.020 mg of isoproterenol/100 g body weight and 0.05 mg of pilocarpine/100 g body weight in the same syringe. Total saliva is then obtained from the oral cavity over a 10-min period using capillary tubes. The mice are treated with three intranasallly administered doses of immunomodulating complexes to be tested at the time of disease. The effect of the treatment is evaluated by comparing the level of saliva production in the treated and untreated mice.

Example 6

Immunomodulating Complexes for the Treatment of Allergic Diseases

Bet v 1 has been identified as one of the major birch allergens, and Phl p 1 and Phl p 5 have been identified as two major grass pollen allergens. The immunodominant peptide epitope of Bet v 1 has been identified as having the peptide sequence MGETLLRAVESY (SEQ ID NO:14). The immunodominant peptide epitope of Phl p 1 has been identified as having the peptide sequence AGELELQFRRVKCKY (SEQ ID NO:15), and the immunodominant peptide epitope of Phl p 5 has been identified as having the peptide sequence TVATAPEVKYTVFETALK (SEQ ID NO:16). DNA encoding these peptide epitopes are cloned into the CTA1-R7K/C187A vector, resulting in vectors comprising DNA constructs encoding the immunomodulating complexes K-CTA1-R7K/C187A-Betv1-DD (SEQ ID NO:17), K-CTA1-R7K/C187A-Phl p1-DD (SEQ ID NO:18), and K-CTA1-R7K/C187A-Phl p5-DD (SEQ ID NO:19), respectively. Expression vectors are transfected into *E. coli* and the expressed immunomodulating complexes are purified using standard techniques.

Example 7

Therapeutic Effects of Immunomodulating Complexes for the Treatment of Allergic Diseases A suitable model for studying the therapeutic effects of immunomodulating complexes for the treatment of allergic disease is e.g. the mouse model of allergic poly-sensitization to the major birch and grass pollen allergens Bet v 1, Phl p 1 and Phl p 5 established by Hufnagl et al. (Clin Exp Allergy, 2008, 38, 1192-1202).

In brief, sensitization is performed by three intraperitoneal (i.p.) immunizations (days 22, 36 and 50) of recombinant Bet v 1, Phl p 1 and Phl p 5 (5 mg each) or a mixture of one or more of these allergens adsorbed to aluminium hydroxide $(Al(OH)_3$ at 14-day intervals. As treatment, one or more of the immunomodulating complexes to be tested are administered (5 mg each) intranasally (i.n.) in 30 mL of 0.9% NaCl three times at 7-day intervals (days 0, 7 and 14) before sensitization. One week after the last i.p. immunization, an aerosol challenge with 1% w/v birch pollen and/or phleum extract is performed on 2 consecutive days. Two days after aerosol challenge (day 60), the mice are killed, and bronchoalveolar lavages (BAL) are collected. Airway inflammation is determined by the number of inflammatory cells (macrophages, lymphocytes, eosinophils) and IL-5 levels in BAL fluids. Effect of treatment is seen as significantly reduced eosinophils and IL-5 in BAL in mice treated with immunomodulating complexes as compared to control mice.

Example 8

Dimer Formation of CTA1-R7K-COL-DD and K-CTA1-R7K/C187A-COL-DD

Dimer formation of CTA1-R7K-COL-DD and K-CTA1-R7K/C187A-COL-DD was studied using analytical size exclusion chromatography (SEC). An ÄKTAFPLC system (GE Healthcare) equipped with a Superdex 200 HR 10/30 column (GE Healthcare) was used for the study. As the mobile phase, 10 mM Na-phosphate buffer pH 7.4, 0.4 M NaCl was used, at a flow rate of 0.4 ml/min at room temperature. The samples were CTA1-R7K-COL-DD (Batch 091118, 2.4 mg/mL) and K-CTA1-R7K/C187A-COL-DD (Batch 091118, 5.6 mg/mL). The samples were thawed from −80° C. and diluted to 1.5 mg/mL in buffer before analysis. 50 μL was injected onto the column. Purity of the preparations was analyzed by SDS-PAGE followed by Coomassie staining on a NuPAGE 4-12% Bis-Tris gel (Invitrogen) under reducing conditions.

Results

Figure 4:
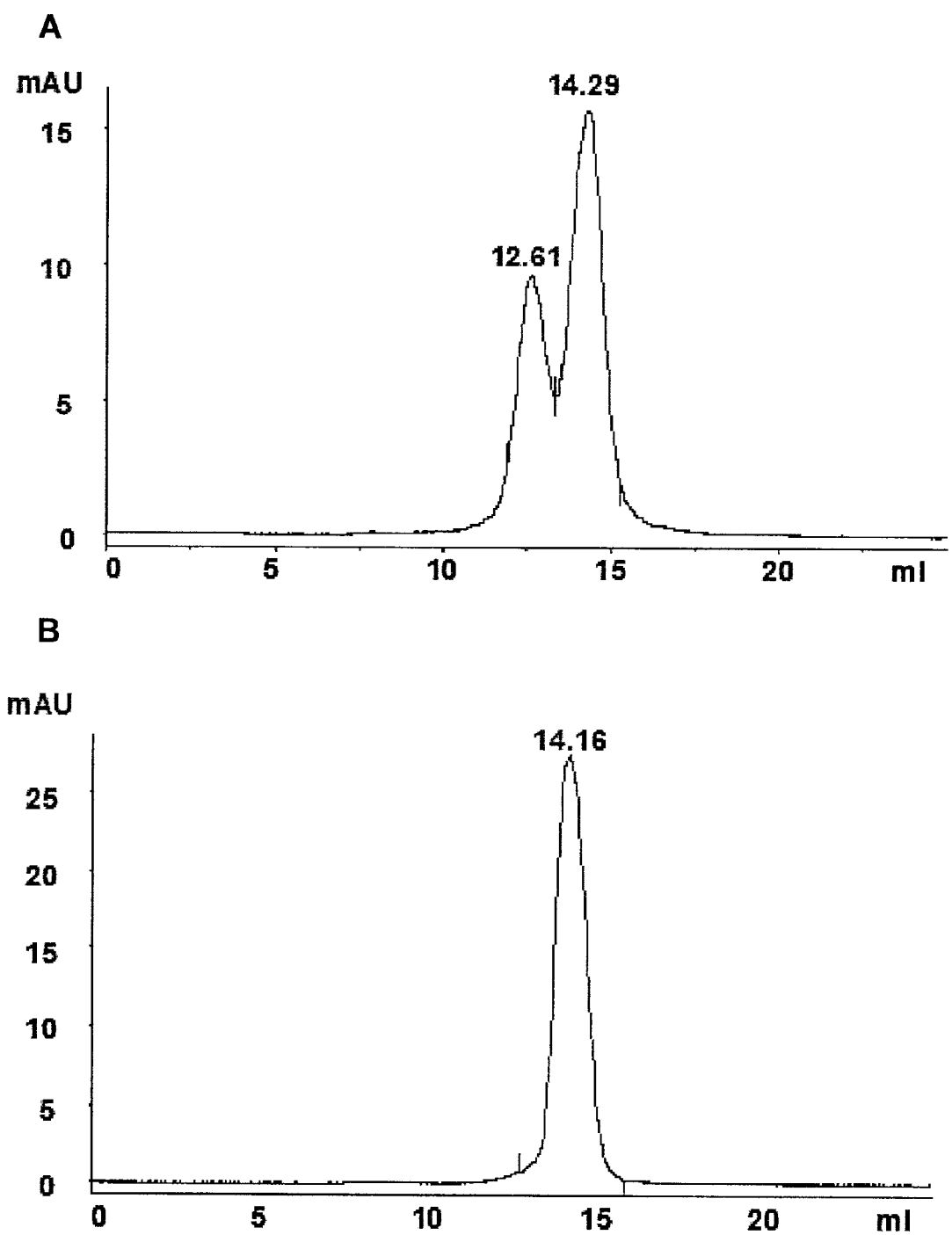
Figure 5:

As seen from the SEC analysis, a significant amount of dimers had been formed and could be identified in the CTA1-R7K-COL-DD sample (FIG. 4A). Dimers can be seen eluting as a peak at 12.61 ml, and monomers as a peak at 14.29 ml. In comparison, no dimers could be detected in the K-CTA1-R7K/C187A-COL-DD sample (FIG. 4B), indicated as a single peak of monomers eluting at 14.16 ml. As can be seen from FIG. 5, the two preparations are equally pure and composed of only one component under reducing condition, i.e. the monomeric immunomodulation complex.

Example 9

Comparison of Levels of Productivity

The yield of purified material from 1 g of bacterial pellet following cultivation of recombinant *E. coli* strains carrying plasmids encoding different immunomodulating complexes according to the invention is listed in Table 3.

TABLE 3

Comparison of levels of productivity

| Complex | Yield |
|---|---|
| CTA1-R7K-DD | 0.94 mg |
| K-CTA1-R7K/C187A-DD | 4.03 mg |
| CTA1-R7K-COL-DD | 0.88 mg |
| K-CTA1-R9K/C187A-COL-DD | 4.47 mg |

As can be seen from Table 3, the productivity is significantly higher for the complexes comprising the K insertion and the C187A mutation.

The invention claimed is:

1. An immunomodulating complex being a fusion protein comprising:
   (a) a mutant subunit of the ADP-ribosylating A1-subunit of the cholera toxin (CTA1) that is the that is the K-CTA1-R7K/C187A mutant having the amino acid sequence of SEQ ID NO:2,
   (b) a peptide capable of binding to a specific cellular receptor, wherein said peptide is a dimer of a Protein A D-subunit; and
   (c) one or more epitopes associated with an autoimmune disease, wherein, the one or more epitopes are autoimmune epitopes associated with an autoimmune disease, and
   wherein the autoimmune disease is selected from the group consisting of insulin-dependent diabetes mellitus, multiple sclerosis, rheumatoid arthritis, autoimmune uveitis, primary biliary cirrhosis, myasthenia gravis, Sjögren's syndrome, pemphigus vulgaris, scleroderma, systemic lupus erythematosus, and Grave's disease.

2. The immunomodulating complexes K-CTA1-R7K/C187A-COL-DD (SEQ ID NO:4), CTA1-R7K/C187A-COL-DD (SEQ ID NO:10), K-CTA1-R7K/C187A-Ro169-DD (SEQ ID NO:11), K-CTA1-R7K/C187A-Ro211-DD (SEQ ID NO:12), K-CTA1R7K/C187A-Ro274-DD (SEQ ID NO:13), K-CTA1-R7K/C187A-Betv1-DD (SEQ ID NO:17), K-CTA1-R7K/C187A-Phl p1-DD (SEQ ID NO:18), and K-CTA1-R7K/C187A-Phl p5-DD (SEQ ID NO:19).

3. An immunomodulating complex being a fusion protein comprising:
   (a) a mutant subunit of the ADP-ribosylating A1-subunit of the cholera toxin (CTA1) that is the CTA1-R7K/C187A mutant having the amino acid sequence of SEQ ID NO:1 or that is the K-CTA1-R7K/C187A mutant having the amino acid sequence of SEQ ID NO:2,
   (b) a peptide capable of binding to a specific cellular receptor wherein said peptide is a dimer of a Protein A D-subunit; and
   (c) one or more epitopes associated with an autoimmune disease, wherein, in the mutant CTA1 subunit, the amino acids corresponding to the amino acid 7, arginine, and the amino acid 187, cysteine, in the native CTA1 have been replaced with lysine at amino acid 7 and alanine at amino acid 187.

* * * * *

SEQUENCE LISTING

```
<160> NUMBER OF SEQ ID NOS: 20

<210> SEQ ID NO 1
<211> LENGTH: 194
<212> TYPE: PRT
<213> ORGANISM: Vibrio cholerae
<220> FEATURE:
<221> NAME/KEY: VARIANT
<222> LOCATION: (7)..(7)
<223> OTHER INFORMATION: ARG-LYS MUTATION
<220> FEATURE:
<221> NAME/KEY: VARIANT
<222> LOCATION: (187)..(187)
<223> OTHER INFORMATION: CYS-ALA MUTATION

<400> SEQUENCE: 1

Asn Asp Asp Lys Leu Tyr Lys Ala Asp Ser Arg Pro Pro Asp Glu Ile
1               5                   10                  15

Lys Gln Ser Gly Gly Leu Met Pro Arg Gly Gln Ser Glu Tyr Phe Asp
            20                  25                  30

Arg Gly Thr Gln Met Asn Ile Asn Leu Tyr Asp His Ala Arg Gly Thr
        35                  40                  45

Gln Thr Gly Phe Val Arg His Asp Asp Gly Tyr Val Ser Thr Ser Ile
    50                  55                  60

Ser Leu Arg Ser Ala His Leu Val Gly Gln Thr Ile Leu Ser Gly His
65                  70                  75                  80

Ser Thr Tyr Tyr Ile Tyr Val Ile Ala Thr Ala Pro Asn Met Phe Asn
                85                  90                  95

Val Asn Asp Val Leu Gly Ala Tyr Ser Pro His Pro Asp Glu Gln Glu
            100                 105                 110

Val Ser Ala Leu Gly Gly Ile Pro Tyr Ser Gln Ile Tyr Gly Trp Tyr
        115                 120                 125

Arg Val His Phe Gly Val Leu Asp Glu Gln Leu His Arg Asn Arg Gly
    130                 135                 140
```

Tyr Arg Asp Arg Tyr Tyr Ser Asn Leu Asp Ile Ala Pro Ala Ala Asp
145                 150                 155                 160

Gly Tyr Gly Leu Ala Gly Phe Pro Pro Glu His Arg Ala Trp Arg Glu
            165                 170                 175

Glu Pro Trp Ile His His Ala Pro Pro Gly Ala Gly Asn Ala Pro Arg
            180                 185                 190

Ser Ser

<210> SEQ ID NO 2
<211> LENGTH: 195
<212> TYPE: PRT
<213> ORGANISM: Vibrio cholerae
<220> FEATURE:
<221> NAME/KEY: Variant
<222> LOCATION: (1)..(1)
<223> OTHER INFORMATION: LYS INSERTION
<220> FEATURE:
<221> NAME/KEY: Variant
<222> LOCATION: (8)..(8)
<223> OTHER INFORMATION: ARG-LYS MUTATION
<220> FEATURE:
<221> NAME/KEY: Variant
<222> LOCATION: (188)..(188)
<223> OTHER INFORMATION: CYS-ALA MUTATION

<400> SEQUENCE: 2

Lys Asn Asp Asp Lys Leu Tyr Lys Ala Asp Ser Arg Pro Pro Asp Glu
1               5                   10                  15

Ile Lys Gln Ser Gly Gly Leu Met Pro Arg Gly Gln Ser Glu Tyr Phe
            20                  25                  30

Asp Arg Gly Thr Gln Met Asn Ile Asn Leu Tyr Asp His Ala Arg Gly
            35                  40                  45

Thr Gln Thr Gly Phe Val Arg His Asp Asp Gly Tyr Val Ser Thr Ser
    50                  55                  60

Ile Ser Leu Arg Ser Ala His Leu Val Gly Gln Thr Ile Leu Ser Gly
65              70                  75                  80

His Ser Thr Tyr Tyr Ile Tyr Val Ile Ala Thr Ala Pro Asn Met Phe
                85                  90                  95

Asn Val Asn Asp Val Leu Gly Ala Tyr Ser Pro His Pro Asp Glu Gln
            100                 105                 110

Glu Val Ser Ala Leu Gly Gly Ile Pro Tyr Ser Gln Ile Tyr Gly Trp
            115                 120                 125

Tyr Arg Val His Phe Gly Val Leu Asp Glu Gln Leu His Arg Asn Arg
        130                 135                 140

Gly Tyr Arg Asp Arg Tyr Tyr Ser Asn Leu Asp Ile Ala Pro Ala Ala
145                 150                 155                 160

Asp Gly Tyr Gly Leu Ala Gly Phe Pro Pro Glu His Arg Ala Trp Arg
                165                 170                 175

Glu Glu Pro Trp Ile His His Ala Pro Pro Gly Ala Gly Asn Ala Pro
            180                 185                 190

Arg Ser Ser
        195

<210> SEQ ID NO 3
<211> LENGTH: 1056
<212> TYPE: DNA
<213> ORGANISM: Artificial
<220> FEATURE:
<223> OTHER INFORMATION: SYNTHETIC FUSION PROTEIN
<220> FEATURE:

<220> NAME/KEY: CDS
<222> LOCATION: (1)..(1056)

<400> SEQUENCE: 3

```
atg aaa aat gat gat aag tta tat aag gca gat tct aga cct cct gat      48
Met Lys Asn Asp Asp Lys Leu Tyr Lys Ala Asp Ser Arg Pro Pro Asp
1               5                   10                  15 gaa ata aag cag tca ggt ggt ctt atg cca aga gga cag agt gag tac      96
Glu Ile Lys Gln Ser Gly Gly Leu Met Pro Arg Gly Gln Ser Glu Tyr
            20                  25                  30 ttt gac cga ggt act caa atg aat atc aac ctt tat gat cat gca aga     144
Phe Asp Arg Gly Thr Gln Met Asn Ile Asn Leu Tyr Asp His Ala Arg
        35                  40                  45 gga act cag acg gga ttt gtt agg cac gat gat gga tat gtt tcc acc     192
Gly Thr Gln Thr Gly Phe Val Arg His Asp Asp Gly Tyr Val Ser Thr
    50                  55                  60 tca att agt ttg aga agt gcc cac tta gtg ggt caa act ata ttg tct     240
Ser Ile Ser Leu Arg Ser Ala His Leu Val Gly Gln Thr Ile Leu Ser
65                  70                  75                  80 ggt cat tct act tat tat ata tat gtt ata gcc act gca ccc aac atg     288
Gly His Ser Thr Tyr Tyr Ile Tyr Val Ile Ala Thr Ala Pro Asn Met
                85                  90                  95 ttt aac gtt aat gat gta tta ggg gca tac agt cct cat cca gat gaa     336
Phe Asn Val Asn Asp Val Leu Gly Ala Tyr Ser Pro His Pro Asp Glu
            100                 105                 110 caa gaa gtt tct gct tta ggt ggg att cca tac tcc caa ata tat gga     384
Gln Glu Val Ser Ala Leu Gly Gly Ile Pro Tyr Ser Gln Ile Tyr Gly
        115                 120                 125 tgg tat cga gtt cat ttt ggg gtg ctt gat gaa caa tta cat cgt aat     432
Trp Tyr Arg Val His Phe Gly Val Leu Asp Glu Gln Leu His Arg Asn
    130                 135                 140 agg ggc tac aga gat aga tat tac agt aac tta gat att gct cca gca     480
Arg Gly Tyr Arg Asp Arg Tyr Tyr Ser Asn Leu Asp Ile Ala Pro Ala
145                 150                 155                 160 gca gat ggt tat gga ttg gca ggt ttc cct ccg gag cat aga gct tgg     528
Ala Asp Gly Tyr Gly Leu Ala Gly Phe Pro Pro Glu His Arg Ala Trp
                165                 170                 175 agg gaa gag ccg tgg att cat cat gca ccg ccg ggt gct ggg aat gct     576
Arg Glu Glu Pro Trp Ile His His Ala Pro Pro Gly Ala Gly Asn Ala
            180                 185                 190 cca aga tca tcg gga tct ggt att gct ggc ttc aaa ggt gaa caa ggc     624
Pro Arg Ser Ser Gly Ser Gly Ile Ala Gly Phe Lys Gly Glu Gln Gly
        195                 200                 205 ccc aag gga gaa cct ggc gga tcc ggg aag aca ccc gag gct gat gcg     672
Pro Lys Gly Glu Pro Gly Gly Ser Gly Lys Thr Pro Glu Ala Asp Ala
    210                 215                 220 caa caa aat aac ttc aac aaa gat caa caa agc gcc ttc tat gaa atc     720
Gln Gln Asn Asn Phe Asn Lys Asp Gln Gln Ser Ala Phe Tyr Glu Ile
225                 230                 235                 240 ttg aac atg cct aac tta aac gaa gcg caa cgt aac ggc ttc att caa     768
Leu Asn Met Pro Asn Leu Asn Glu Ala Gln Arg Asn Gly Phe Ile Gln
                245                 250                 255 agt ctt aaa gac gac cca agc caa agc act aac gtt tta ggt gaa gct     816
Ser Leu Lys Asp Asp Pro Ser Gln Ser Thr Asn Val Leu Gly Glu Ala
            260                 265                 270 aaa aaa tta aac gaa tct caa gca ccc aaa ccc gag gct gat gcg caa     864
Lys Lys Leu Asn Glu Ser Gln Ala Pro Lys Pro Glu Ala Asp Ala Gln
        275                 280                 285 caa aat aac ttc aac aaa gat caa caa agc gcc ttc tat gaa atc ttg     912
Gln Asn Asn Phe Asn Lys Asp Gln Gln Ser Ala Phe Tyr Glu Ile Leu
```

```
                     290                 295                 300
aac atg cct aac tta aac gaa gcg caa cgt aac ggc ttc att caa agt    960
Asn Met Pro Asn Leu Asn Glu Ala Gln Arg Asn Gly Phe Ile Gln Ser
305                 310                 315                 320 ctt aaa gac gac cca agc caa agc act aac gtt tta ggt gaa gct aaa   1008
Leu Lys Asp Asp Pro Ser Gln Ser Thr Asn Val Leu Gly Glu Ala Lys
                325                 330                 335 aaa tta aac gaa tct caa gca ccc aaa ccc gag gta gca ggt cag aat   1056
Lys Leu Asn Glu Ser Gln Ala Pro Lys Pro Glu Val Ala Gly Gln Asn
                340                 345                 350
```

<210> SEQ ID NO 4
<211> LENGTH: 352
<212> TYPE: PRT
<213> ORGANISM: Artificial
<220> FEATURE:
<223> OTHER INFORMATION: Synthetic Construct

<400> SEQUENCE: 4

```
Met Lys Asn Asp Asp Lys Leu Tyr Lys Ala Asp Ser Arg Pro Pro Asp
1               5                   10                  15

Glu Ile Lys Gln Ser Gly Gly Leu Met Pro Arg Gly Gln Ser Glu Tyr
                20                  25                  30

Phe Asp Arg Gly Thr Gln Met Asn Ile Asn Leu Tyr Asp His Ala Arg
            35                  40                  45

Gly Thr Gln Thr Gly Phe Val Arg His Asp Asp Gly Tyr Val Ser Thr
        50                  55                  60

Ser Ile Ser Leu Arg Ser Ala His Leu Val Gly Gln Thr Ile Leu Ser
65                  70                  75                  80

Gly His Ser Thr Tyr Tyr Ile Tyr Val Ile Ala Thr Ala Pro Asn Met
                85                  90                  95

Phe Asn Val Asn Asp Val Leu Gly Ala Tyr Ser Pro His Pro Asp Glu
            100                 105                 110

Gln Glu Val Ser Ala Leu Gly Gly Ile Pro Tyr Ser Gln Ile Tyr Gly
        115                 120                 125

Trp Tyr Arg Val His Phe Gly Val Leu Asp Glu Gln Leu His Arg Asn
130                 135                 140

Arg Gly Tyr Arg Asp Arg Tyr Tyr Ser Asn Leu Asp Ile Ala Pro Ala
145                 150                 155                 160

Ala Asp Gly Tyr Gly Leu Ala Gly Phe Pro Pro Glu His Arg Ala Trp
                165                 170                 175

Arg Glu Glu Pro Trp Ile His His Ala Pro Pro Gly Ala Gly Asn Ala
            180                 185                 190

Pro Arg Ser Ser Gly Ser Gly Ile Ala Gly Phe Lys Gly Glu Gln Gly
        195                 200                 205

Pro Lys Gly Glu Pro Gly Gly Ser Gly Lys Thr Pro Glu Ala Asp Ala
210                 215                 220

Gln Gln Asn Asn Phe Asn Lys Asp Gln Gln Ser Ala Phe Tyr Glu Ile
225                 230                 235                 240

Leu Asn Met Pro Asn Leu Asn Glu Ala Gln Arg Asn Gly Phe Ile Gln
                245                 250                 255

Ser Leu Lys Asp Asp Pro Ser Gln Ser Thr Asn Val Leu Gly Glu Ala
            260                 265                 270

Lys Lys Leu Asn Glu Ser Gln Ala Pro Lys Pro Glu Ala Asp Ala Gln
        275                 280                 285

Gln Asn Asn Phe Asn Lys Asp Gln Gln Ser Ala Phe Tyr Glu Ile Leu
```

```
                290                 295                 300
Asn Met Pro Asn Leu Asn Glu Ala Gln Arg Asn Gly Phe Ile Gln Ser
305                 310                 315                 320

Leu Lys Asp Asp Pro Ser Gln Ser Thr Asn Val Leu Gly Glu Ala Lys
            325                 330                 335

Lys Leu Asn Glu Ser Gln Ala Pro Lys Pro Glu Val Ala Gly Gln Asn
        340                 345                 350

<210> SEQ ID NO 5
<211> LENGTH: 14
<212> TYPE: PRT
<213> ORGANISM: Artificial
<220> FEATURE:
<223> OTHER INFORMATION: Peptide derived from collagen II

<400> SEQUENCE: 5

Ile Ala Gly Phe Lys Gly Glu Gln Gly Pro Lys Gly Glu Pro
1               5                   10

<210> SEQ ID NO 6
<211> LENGTH: 21
<212> TYPE: PRT
<213> ORGANISM: Artificial
<220> FEATURE:
<223> OTHER INFORMATION: Peptide dervide from Ro/SSA

<400> SEQUENCE: 6

Thr Lys Tyr Lys Gln Arg Asn Gly Trp Ser His Lys Asp Leu Leu Arg
1               5                   10                  15

Ser His Leu Lys Pro
            20

<210> SEQ ID NO 7
<211> LENGTH: 22
<212> TYPE: PRT
<213> ORGANISM: Artificial
<220> FEATURE:
<223> OTHER INFORMATION: Peptide derived from Ro/SSA

<400> SEQUENCE: 7

Glu Leu Tyr Lys Glu Lys Ala Leu Ser Val Glu Thr Glu Lys Leu Leu
1               5                   10                  15

Lys Tyr Leu Glu Ala Val
            20

<210> SEQ ID NO 8
<211> LENGTH: 16
<212> TYPE: PRT
<213> ORGANISM: Artificial Sequence
<220> FEATURE:
<223> OTHER INFORMATION: Peptide derived from Ro/SSA

<400> SEQUENCE: 8

Gln Glu Met Pro Leu Thr Ala Leu Leu Arg Asn Leu Gly Lys Met Thr
1               5                   10                  15

<210> SEQ ID NO 9
<211> LENGTH: 1050
<212> TYPE: DNA
<213> ORGANISM: Artificial Sequence
<220> FEATURE:
<223> OTHER INFORMATION: SYNTHETIC FUSION PROTEIN
<220> FEATURE:
<221> NAME/KEY: CDS
<222> LOCATION: (1)..(1050)
```

<400> SEQUENCE: 9

```
atg gat gat aag tta tat aag gca gat tct aga cct cct gat gaa ata    48
Met Asp Asp Lys Leu Tyr Lys Ala Asp Ser Arg Pro Pro Asp Glu Ile
1               5                   10                  15 aag cag tca ggt ggt ctt atg cca aga gga cag agt gag tac ttt gac    96
Lys Gln Ser Gly Gly Leu Met Pro Arg Gly Gln Ser Glu Tyr Phe Asp
            20                  25                  30 cga ggt act caa atg aat atc aac ctt tat gat cat gca aga gga act   144
Arg Gly Thr Gln Met Asn Ile Asn Leu Tyr Asp His Ala Arg Gly Thr
        35                  40                  45 cag acg gga ttt gtt agg cac gat gat gga tat gtt tcc acc tca att   192
Gln Thr Gly Phe Val Arg His Asp Asp Gly Tyr Val Ser Thr Ser Ile
    50                  55                  60 agt ttg aga agt gcc cac tta gtg ggt caa act ata ttg tct ggt cat   240
Ser Leu Arg Ser Ala His Leu Val Gly Gln Thr Ile Leu Ser Gly His
65                  70                  75                  80 tct act tat tat ata tat gtt ata gcc act gca ccc aac atg ttt aac   288
Ser Thr Tyr Tyr Ile Tyr Val Ile Ala Thr Ala Pro Asn Met Phe Asn
                85                  90                  95 gtt aat gat gta tta ggg gca tac agt cct cat cca gat gaa caa gaa   336
Val Asn Asp Val Leu Gly Ala Tyr Ser Pro His Pro Asp Glu Gln Glu
            100                 105                 110 gtt tct gct tta ggt ggg att cca tac tcc caa ata tat gga tgg tat   384
Val Ser Ala Leu Gly Gly Ile Pro Tyr Ser Gln Ile Tyr Gly Trp Tyr
        115                 120                 125 cga gtt cat ttt ggg gtg ctt gat gaa caa tta cat cgt aat agg ggc   432
Arg Val His Phe Gly Val Leu Asp Glu Gln Leu His Arg Asn Arg Gly
    130                 135                 140 tac aga gat aga tat tac agt aac tta gat att gct cca gca gca gat   480
Tyr Arg Asp Arg Tyr Tyr Ser Asn Leu Asp Ile Ala Pro Ala Ala Asp
145                 150                 155                 160 ggt tat gga ttg gca ggt ttc cct ccg gag cat aga gct tgg agg gaa   528
Gly Tyr Gly Leu Ala Gly Phe Pro Pro Glu His Arg Ala Trp Arg Glu
                165                 170                 175 gag ccg tgg att cat cat gca ccg ccg ggt gct ggg aat gct cca aga   576
Glu Pro Trp Ile His His Ala Pro Pro Gly Ala Gly Asn Ala Pro Arg
            180                 185                 190 tca tcg gga tct ggt att gct ggc ttc aaa ggt gaa caa ggc ccc aag   624
Ser Ser Gly Ser Gly Ile Ala Gly Phe Lys Gly Glu Gln Gly Pro Lys
        195                 200                 205 gga gaa cct ggc gga tcc ggg aag aca ccc gag gct gat gcg caa caa   672
Gly Glu Pro Gly Gly Ser Gly Lys Thr Pro Glu Ala Asp Ala Gln Gln
    210                 215                 220 aat aac ttc aac aaa gat caa caa agc gcc ttc tat gaa atc ttg aac   720
Asn Asn Phe Asn Lys Asp Gln Gln Ser Ala Phe Tyr Glu Ile Leu Asn
225                 230                 235                 240 atg cct aac tta aac gaa gcg caa cgt aac ggc ttc att caa agt ctt   768
Met Pro Asn Leu Asn Glu Ala Gln Arg Asn Gly Phe Ile Gln Ser Leu
                245                 250                 255 aaa gac gac cca agc caa agc act aac gtt tta ggt gaa gct aaa aaa   816
Lys Asp Asp Pro Ser Gln Ser Thr Asn Val Leu Gly Glu Ala Lys Lys
            260                 265                 270 tta aac gaa tct caa gca ccc aaa ccc gag gct gat gcg caa caa aat   864
Leu Asn Glu Ser Gln Ala Pro Lys Pro Glu Ala Asp Ala Gln Gln Asn
        275                 280                 285 aac ttc aac aaa gat caa caa agc gcc ttc tat gaa atc ttg aac atg   912
Asn Phe Asn Lys Asp Gln Gln Ser Ala Phe Tyr Glu Ile Leu Asn Met
    290                 295                 300
```

| | | | | | | | | | | | | | | |
|---|---|---|---|---|---|---|---|---|---|---|---|---|---|---|
| cct | aac | tta | aac | gaa | gcg | caa | cgt | aac | ggc | ttc | att | caa | agt | ctt | aaa | 960 |
| Pro | Asn | Leu | Asn | Glu | Ala | Gln | Arg | Asn | Gly | Phe | Ile | Gln | Ser | Leu | Lys | |
| 305 | | | | 310 | | | | | 315 | | | | | 320 | | |
| gac | gac | cca | agc | caa | agc | act | aac | gtt | tta | ggt | gaa | gct | aaa | aaa | tta | 1008 |
| Asp | Asp | Pro | Ser | Gln | Ser | Thr | Asn | Val | Leu | Gly | Glu | Ala | Lys | Lys | Leu | |
| | | | | 325 | | | | | 330 | | | | | 335 | | |
| aac | gaa | tct | caa | gca | ccc | aaa | ccc | gag | gta | gca | ggt | cag | aat | | | 1050 |
| Asn | Glu | Ser | Gln | Ala | Pro | Lys | Pro | Glu | Val | Ala | Gly | Gln | Asn | | | |
| | | | | 340 | | | | 345 | | | | | 350 | | | |

<210> SEQ ID NO 10
<211> LENGTH: 350
<212> TYPE: PRT
<213> ORGANISM: Artificial Sequence
<220> FEATURE:
<223> OTHER INFORMATION: Synthetic Construct

<400> SEQUENCE: 10

Met Asp Asp Lys Leu Tyr Lys Ala Asp Ser Arg Pro Pro Asp Glu Ile
1               5                   10                  15

Lys Gln Ser Gly Gly Leu Met Pro Arg Gly Gln Ser Glu Tyr Phe Asp
            20                  25                  30

Arg Gly Thr Gln Met Asn Ile Asn Leu Tyr Asp His Ala Arg Gly Thr
        35                  40                  45

Gln Thr Gly Phe Val Arg His Asp Asp Gly Tyr Val Ser Thr Ser Ile
    50                  55                  60

Ser Leu Arg Ser Ala His Leu Val Gly Gln Thr Ile Leu Ser Gly His
65                  70                  75                  80

Ser Thr Tyr Tyr Ile Tyr Val Ile Ala Thr Ala Pro Asn Met Phe Asn
                85                  90                  95

Val Asn Asp Val Leu Gly Ala Tyr Ser Pro His Pro Asp Glu Gln Glu
            100                 105                 110

Val Ser Ala Leu Gly Gly Ile Pro Tyr Ser Gln Ile Tyr Gly Trp Tyr
        115                 120                 125

Arg Val His Phe Gly Val Leu Asp Glu Gln Leu His Arg Asn Arg Gly
    130                 135                 140

Tyr Arg Asp Arg Tyr Tyr Ser Asn Leu Asp Ile Ala Pro Ala Ala Asp
145                 150                 155                 160

Gly Tyr Gly Leu Ala Gly Phe Pro Pro Glu His Arg Ala Trp Arg Glu
                165                 170                 175

Glu Pro Trp Ile His His Ala Pro Pro Gly Ala Gly Asn Ala Pro Arg
            180                 185                 190

Ser Ser Gly Ser Gly Ile Ala Gly Phe Lys Gly Glu Gln Gly Pro Lys
        195                 200                 205

Gly Glu Pro Gly Gly Ser Gly Lys Thr Pro Glu Ala Asp Ala Gln Gln
    210                 215                 220

Asn Asn Phe Asn Lys Asp Gln Gln Ser Ala Phe Tyr Glu Ile Leu Asn
225                 230                 235                 240

Met Pro Asn Leu Asn Glu Ala Gln Arg Asn Gly Phe Ile Gln Ser Leu
                245                 250                 255

Lys Asp Asp Pro Ser Gln Ser Thr Asn Val Leu Gly Glu Ala Lys Lys
            260                 265                 270

Leu Asn Glu Ser Gln Ala Pro Lys Pro Glu Ala Asp Ala Gln Gln Asn
        275                 280                 285

Asn Phe Asn Lys Asp Gln Gln Ser Ala Phe Tyr Glu Ile Leu Asn Met
    290                 295                 300

Pro Asn Leu Asn Glu Ala Gln Arg Asn Gly Phe Ile Gln Ser Leu Lys
305                 310                 315                 320

Asp Asp Pro Ser Gln Ser Thr Asn Val Leu Gly Glu Ala Lys Lys Leu
            325                 330                 335

Asn Glu Ser Gln Ala Pro Lys Pro Glu Val Ala Gly Gln Asn
            340                 345                 350

<210> SEQ ID NO 11
<211> LENGTH: 357
<212> TYPE: PRT
<213> ORGANISM: Artificial Sequence
<220> FEATURE:
<223> OTHER INFORMATION: SYNTHETIC FUSION PROTEIN

<400> SEQUENCE: 11

Met Lys Asn Asp Asp Lys Leu Tyr Lys Ala Asp Ser Arg Pro Pro Asp
1               5                   10                  15

Glu Ile Lys Gln Ser Gly Gly Leu Met Pro Arg Gly Gln Ser Glu Tyr
            20                  25                  30

Phe Asp Arg Gly Thr Gln Met Asn Ile Asn Leu Tyr Asp His Ala Arg
        35                  40                  45

Gly Thr Gln Thr Gly Phe Val Arg His Asp Asp Gly Tyr Val Ser Thr
50                  55                  60

Ser Ile Ser Leu Arg Ser Ala His Leu Val Gly Gln Thr Ile Leu Ser
65                  70                  75                  80

Gly His Ser Thr Tyr Tyr Ile Tyr Val Ile Ala Thr Ala Pro Asn Met
                85                  90                  95

Phe Asn Val Asn Asp Val Leu Gly Ala Tyr Ser Pro His Pro Asp Glu
            100                 105                 110

Gln Glu Val Ser Ala Leu Gly Gly Ile Pro Tyr Ser Gln Ile Tyr Gly
        115                 120                 125

Trp Tyr Arg Val His Phe Gly Val Leu Asp Glu Gln Leu His Arg Asn
130                 135                 140

Arg Gly Tyr Arg Asp Arg Tyr Tyr Ser Asn Leu Asp Ile Ala Pro Ala
145                 150                 155                 160

Ala Asp Gly Tyr Gly Leu Ala Gly Phe Pro Pro Glu His Arg Ala Trp
                165                 170                 175

Arg Glu Glu Pro Trp Ile His His Ala Pro Pro Gly Ala Gly Asn Ala
            180                 185                 190

Pro Arg Ser Ser Gly Ser Thr Lys Tyr Lys Gln Arg Asn Gly Trp Ser
        195                 200                 205

His Lys Asp Leu Leu Arg Ser His Leu Lys Pro Gly Ser Gly Lys Thr
210                 215                 220

Pro Glu Ala Asp Ala Gln Gln Asn Asn Phe Asn Lys Asp Gln Gln Ser
225                 230                 235                 240

Ala Phe Tyr Glu Ile Leu Asn Met Pro Asn Leu Asn Glu Ala Gln Arg
                245                 250                 255

Asn Gly Phe Ile Gln Ser Leu Lys Asp Asp Pro Ser Gln Ser Thr Asn
            260                 265                 270

Val Leu Gly Glu Ala Lys Lys Leu Asn Glu Ser Gln Ala Pro Lys Pro
        275                 280                 285

Glu Ala Asp Ala Gln Gln Asn Asn Phe Asn Lys Asp Gln Gln Ser Ala
290                 295                 300

Phe Tyr Glu Ile Leu Asn Met Pro Asn Leu Asn Glu Ala Gln Arg Asn
305                 310                 315                 320

Gly Phe Ile Gln Ser Leu Lys Asp Asp Pro Ser Gln Ser Thr Asn Val
              325                 330                 335

Leu Gly Glu Ala Lys Lys Leu Asn Glu Ser Gln Ala Pro Lys Pro Glu
          340                 345                 350

Val Ala Gly Gln Asn
        355

<210> SEQ ID NO 12
<211> LENGTH: 358
<212> TYPE: PRT
<213> ORGANISM: Artificial Sequence
<220> FEATURE:
<223> OTHER INFORMATION: SYNTHETIC FUSION PROTEIN

<400> SEQUENCE: 12

Met Lys Asn Asp Asp Lys Leu Tyr Lys Ala Asp Ser Arg Pro Pro Asp
1               5                   10                  15

Glu Ile Lys Gln Ser Gly Gly Leu Met Pro Arg Gly Gln Ser Glu Tyr
            20                  25                  30

Phe Asp Arg Gly Thr Gln Met Asn Ile Asn Leu Tyr Asp His Ala Arg
        35                  40                  45

Gly Thr Gln Thr Gly Phe Val Arg His Asp Asp Gly Tyr Val Ser Thr
    50                  55                  60

Ser Ile Ser Leu Arg Ser Ala His Leu Val Gly Gln Thr Ile Leu Ser
65                  70                  75                  80

Gly His Ser Thr Tyr Tyr Ile Tyr Val Ile Ala Thr Ala Pro Asn Met
                85                  90                  95

Phe Asn Val Asn Asp Val Leu Gly Ala Tyr Ser Pro His Pro Asp Glu
            100                 105                 110

Gln Glu Val Ser Ala Leu Gly Gly Ile Pro Tyr Ser Gln Ile Tyr Gly
        115                 120                 125

Trp Tyr Arg Val His Phe Gly Val Leu Asp Glu Gln Leu His Arg Asn
    130                 135                 140

Arg Gly Tyr Arg Asp Arg Tyr Tyr Ser Asn Leu Asp Ile Ala Pro Ala
145                 150                 155                 160

Ala Asp Gly Tyr Gly Leu Ala Gly Phe Pro Pro Glu His Arg Ala Trp
                165                 170                 175

Arg Glu Glu Pro Trp Ile His His Ala Pro Pro Gly Ala Gly Asn Ala
            180                 185                 190

Pro Arg Ser Ser Gly Ser Glu Leu Tyr Lys Glu Lys Ala Leu Ser Val
        195                 200                 205

Glu Thr Glu Lys Leu Leu Lys Tyr Leu Glu Ala Val Gly Ser Gly Lys
    210                 215                 220

Thr Pro Glu Ala Asp Ala Gln Gln Asn Asn Phe Asn Lys Asp Gln Gln
225                 230                 235                 240

Ser Ala Phe Tyr Glu Ile Leu Asn Met Pro Asn Leu Asn Glu Ala Gln
                245                 250                 255

Arg Asn Gly Phe Ile Gln Ser Leu Lys Asp Asp Pro Ser Gln Ser Thr
            260                 265                 270

Asn Val Leu Gly Glu Ala Lys Lys Leu Asn Glu Ser Gln Ala Pro Lys
        275                 280                 285

Pro Glu Ala Asp Ala Gln Gln Asn Asn Phe Asn Lys Asp Gln Gln Ser
    290                 295                 300

Ala Phe Tyr Glu Ile Leu Asn Met Pro Asn Leu Asn Glu Ala Gln Arg
305                 310                 315                 320

```
Asn Gly Phe Ile Gln Ser Leu Lys Asp Asp Pro Ser Gln Ser Thr Asn
                325                 330                 335

Val Leu Gly Glu Ala Lys Lys Leu Asn Glu Ser Gln Ala Pro Lys Pro
            340                 345                 350

Glu Val Ala Gly Gln Asn
            355

<210> SEQ ID NO 13
<211> LENGTH: 352
<212> TYPE: PRT
<213> ORGANISM: Artificial Sequence
<220> FEATURE:
<223> OTHER INFORMATION: SYNTHETIC FUSION PROTEIN

<400> SEQUENCE: 13

Met Lys Asn Asp Asp Lys Leu Tyr Lys Ala Asp Ser Arg Pro Pro Asp
1               5                   10                  15

Glu Ile Lys Gln Ser Gly Gly Leu Met Pro Arg Gly Gln Ser Glu Tyr
            20                  25                  30

Phe Asp Arg Gly Thr Gln Met Asn Ile Asn Leu Tyr Asp His Ala Arg
        35                  40                  45

Gly Thr Gln Thr Gly Phe Val Arg His Asp Asp Gly Tyr Val Ser Thr
    50                  55                  60

Ser Ile Ser Leu Arg Ser Ala His Leu Val Gly Gln Thr Ile Leu Ser
65                  70                  75                  80

Gly His Ser Thr Tyr Tyr Ile Tyr Val Ile Ala Thr Ala Pro Asn Met
                85                  90                  95

Phe Asn Val Asn Asp Val Leu Gly Ala Tyr Ser Pro His Pro Asp Glu
            100                 105                 110

Gln Glu Val Ser Ala Leu Gly Gly Ile Pro Tyr Ser Gln Ile Tyr Gly
        115                 120                 125

Trp Tyr Arg Val His Phe Gly Val Leu Asp Glu Gln Leu His Arg Asn
130                 135                 140

Arg Gly Tyr Arg Asp Arg Tyr Tyr Ser Asn Leu Asp Ile Ala Pro Ala
145                 150                 155                 160

Ala Asp Gly Tyr Gly Leu Ala Gly Phe Pro Pro Glu His Arg Ala Trp
                165                 170                 175

Arg Glu Glu Pro Trp Ile His His Ala Pro Pro Gly Ala Gly Asn Ala
            180                 185                 190

Pro Arg Ser Ser Gly Ser Gln Glu Met Pro Leu Thr Ala Leu Leu Arg
        195                 200                 205

Asn Leu Gly Lys Met Thr Gly Ser Gly Lys Thr Pro Glu Ala Asp Ala
    210                 215                 220

Gln Gln Asn Asn Phe Asn Lys Asp Gln Gln Ser Ala Phe Tyr Glu Ile
225                 230                 235                 240

Leu Asn Met Pro Asn Leu Asn Glu Ala Gln Arg Asn Gly Phe Ile Gln
                245                 250                 255

Ser Leu Lys Asp Asp Pro Ser Gln Ser Thr Asn Val Leu Gly Glu Ala
            260                 265                 270

Lys Lys Leu Asn Glu Ser Gln Ala Pro Lys Pro Glu Ala Asp Ala Gln
        275                 280                 285

Gln Asn Asn Phe Asn Lys Asp Gln Gln Ser Ala Phe Tyr Glu Ile Leu
    290                 295                 300

Asn Met Pro Asn Leu Asn Glu Ala Gln Arg Asn Gly Phe Ile Gln Ser
305                 310                 315                 320
```

```
Leu Lys Asp Asp Pro Ser Gln Ser Thr Asn Val Leu Gly Glu Ala Lys
            325                 330                 335

Lys Leu Asn Glu Ser Gln Ala Pro Lys Pro Glu Val Ala Gly Gln Asn
        340                 345                 350

<210> SEQ ID NO 14
<211> LENGTH: 12
<212> TYPE: PRT
<213> ORGANISM: Artificial Sequence
<220> FEATURE:
<223> OTHER INFORMATION: Peptide derived from Bet v 1

<400> SEQUENCE: 14

Met Gly Glu Thr Leu Leu Arg Ala Val Glu Ser Tyr
1               5                   10

<210> SEQ ID NO 15
<211> LENGTH: 15
<212> TYPE: PRT
<213> ORGANISM: Artificial Sequence
<220> FEATURE:
<223> OTHER INFORMATION: Peptide derived from Phl p 1

<400> SEQUENCE: 15

Ala Gly Glu Leu Glu Leu Gln Phe Arg Arg Val Lys Cys Lys Tyr
1               5                   10                  15

<210> SEQ ID NO 16
<211> LENGTH: 18
<212> TYPE: PRT
<213> ORGANISM: Artificial Sequence
<220> FEATURE:
<223> OTHER INFORMATION: Peptide derived from Phl p 5

<400> SEQUENCE: 16

Thr Val Ala Thr Ala Pro Glu Val Lys Tyr Thr Val Phe Glu Thr Ala
1               5                   10                  15

Leu Lys

<210> SEQ ID NO 17
<211> LENGTH: 348
<212> TYPE: PRT
<213> ORGANISM: Artificial Sequence
<220> FEATURE:
<223> OTHER INFORMATION: SYNTHETIC FUSION PROTEIN

<400> SEQUENCE: 17

Met Lys Asn Asp Asp Lys Leu Tyr Lys Ala Asp Ser Arg Pro Pro Asp
1               5                   10                  15

Glu Ile Lys Gln Ser Gly Gly Leu Met Pro Arg Gly Gln Ser Glu Tyr
            20                  25                  30

Phe Asp Arg Gly Thr Gln Met Asn Ile Asn Leu Tyr Asp His Ala Arg
        35                  40                  45

Gly Thr Gln Thr Gly Phe Val Arg His Asp Asp Gly Tyr Val Ser Thr
    50                  55                  60

Ser Ile Ser Leu Arg Ser Ala His Leu Val Gly Gln Thr Ile Leu Ser
65                  70                  75                  80

Gly His Ser Thr Tyr Tyr Ile Tyr Val Ile Ala Thr Ala Pro Asn Met
                85                  90                  95

Phe Asn Val Asn Asp Val Leu Gly Ala Tyr Ser Pro His Pro Asp Glu
            100                 105                 110

Gln Glu Val Ser Ala Leu Gly Gly Ile Pro Tyr Ser Gln Ile Tyr Gly
```

```
                115                 120                 125

Trp Tyr Arg Val His Phe Gly Val Leu Asp Glu Gln Leu His Arg Asn
130                 135                 140

Arg Gly Tyr Arg Asp Arg Tyr Tyr Ser Asn Leu Asp Ile Ala Pro Ala
145                 150                 155                 160

Ala Asp Gly Tyr Gly Leu Ala Gly Phe Pro Pro Glu His Arg Ala Trp
                165                 170                 175

Arg Glu Glu Pro Trp Ile His His Ala Pro Pro Gly Ala Gly Asn Ala
                180                 185                 190

Pro Arg Ser Ser Gly Ser Met Gly Glu Thr Leu Leu Arg Ala Val Glu
                195                 200                 205

Ser Tyr Gly Ser Gly Lys Thr Pro Glu Ala Asp Ala Gln Gln Asn Asn
210                 215                 220

Phe Asn Lys Asp Gln Gln Ser Ala Phe Tyr Glu Ile Leu Asn Met Pro
225                 230                 235                 240

Asn Leu Asn Glu Ala Gln Arg Asn Gly Phe Ile Gln Ser Leu Lys Asp
                245                 250                 255

Asp Pro Ser Gln Ser Thr Asn Val Leu Gly Glu Ala Lys Lys Leu Asn
                260                 265                 270

Glu Ser Gln Ala Pro Lys Pro Glu Ala Asp Ala Gln Gln Asn Asn Phe
                275                 280                 285

Asn Lys Asp Gln Gln Ser Ala Phe Tyr Glu Ile Leu Asn Met Pro Asn
290                 295                 300

Leu Asn Glu Ala Gln Arg Asn Gly Phe Ile Gln Ser Leu Lys Asp Asp
305                 310                 315                 320

Pro Ser Gln Ser Thr Asn Val Leu Gly Glu Ala Lys Lys Leu Asn Glu
                325                 330                 335

Ser Gln Ala Pro Lys Pro Glu Val Ala Gly Gln Asn
                340                 345

<210> SEQ ID NO 18
<211> LENGTH: 351
<212> TYPE: PRT
<213> ORGANISM: Artificial Sequence
<220> FEATURE:
<223> OTHER INFORMATION: SYNTHETIC FUSION PROTEIN

<400> SEQUENCE: 18

Met Lys Asn Asp Asp Lys Leu Tyr Lys Ala Asp Ser Arg Pro Pro Asp
1               5                   10                  15

Glu Ile Lys Gln Ser Gly Gly Leu Met Pro Arg Gly Gln Ser Glu Tyr
                20                  25                  30

Phe Asp Arg Gly Thr Gln Met Asn Ile Asn Leu Tyr Asp His Ala Arg
            35                  40                  45

Gly Thr Gln Thr Gly Phe Val Arg His Asp Asp Gly Tyr Val Ser Thr
50                  55                  60

Ser Ile Ser Leu Arg Ser Ala His Leu Val Gly Gln Thr Ile Leu Ser
65                  70                  75                  80

Gly His Ser Thr Tyr Tyr Ile Tyr Val Ile Ala Thr Ala Pro Asn Met
                85                  90                  95

Phe Asn Val Asn Asp Val Leu Gly Ala Tyr Ser Pro His Pro Asp Glu
                100                 105                 110

Gln Glu Val Ser Ala Leu Gly Gly Ile Pro Tyr Ser Gln Ile Tyr Gly
            115                 120                 125

Trp Tyr Arg Val His Phe Gly Val Leu Asp Glu Gln Leu His Arg Asn
```

```
                130                 135                 140
Arg Gly Tyr Arg Asp Arg Tyr Tyr Ser Asn Leu Asp Ile Ala Pro Ala
145                 150                 155                 160

Ala Asp Gly Tyr Gly Leu Ala Gly Phe Pro Glu His Arg Ala Trp
                165                 170                 175

Arg Glu Glu Pro Trp Ile His His Ala Pro Pro Gly Ala Gly Asn Ala
                180                 185                 190

Pro Arg Ser Ser Gly Ser Ala Gly Glu Leu Glu Leu Gln Phe Arg Arg
                195                 200                 205

Val Lys Cys Lys Tyr Gly Ser Gly Lys Thr Pro Glu Ala Asp Ala Gln
                210                 215                 220

Gln Asn Asn Phe Asn Lys Asp Gln Gln Ser Ala Phe Tyr Glu Ile Leu
225                 230                 235                 240

Asn Met Pro Asn Leu Asn Glu Ala Gln Arg Asn Gly Phe Ile Gln Ser
                245                 250                 255

Leu Lys Asp Asp Pro Ser Gln Ser Thr Asn Val Leu Gly Glu Ala Lys
                260                 265                 270

Lys Leu Asn Glu Ser Gln Ala Pro Lys Pro Glu Ala Asp Ala Gln Gln
                275                 280                 285

Asn Asn Phe Asn Lys Asp Gln Gln Ser Ala Phe Tyr Glu Ile Leu Asn
                290                 295                 300

Met Pro Asn Leu Asn Glu Ala Gln Arg Asn Gly Phe Ile Gln Ser Leu
305                 310                 315                 320

Lys Asp Asp Pro Ser Gln Ser Thr Asn Val Leu Gly Glu Ala Lys Lys
                325                 330                 335

Leu Asn Glu Ser Gln Ala Pro Lys Pro Glu Val Ala Gly Gln Asn
                340                 345                 350

<210> SEQ ID NO 19
<211> LENGTH: 354
<212> TYPE: PRT
<213> ORGANISM: Artificial Sequence
<220> FEATURE:
<223> OTHER INFORMATION: SYNTHETIC FUSION PROTEIN

<400> SEQUENCE: 19

Met Lys Asn Asp Asp Lys Leu Tyr Lys Ala Asp Ser Arg Pro Pro Asp
1               5                   10                  15

Glu Ile Lys Gln Ser Gly Gly Leu Met Pro Arg Gly Gln Ser Glu Tyr
                20                  25                  30

Phe Asp Arg Gly Thr Gln Met Asn Ile Asn Leu Tyr Asp His Ala Arg
                35                  40                  45

Gly Thr Gln Thr Gly Phe Val Arg His Asp Asp Gly Tyr Val Ser Thr
                50                  55                  60

Ser Ile Ser Leu Arg Ser Ala His Leu Val Gly Gln Thr Ile Leu Ser
65                  70                  75                  80

Gly His Ser Thr Tyr Tyr Ile Tyr Val Ile Ala Thr Ala Pro Asn Met
                85                  90                  95

Phe Asn Val Asn Asp Val Leu Gly Ala Tyr Ser Pro His Pro Asp Glu
                100                 105                 110

Gln Glu Val Ser Ala Leu Gly Gly Ile Pro Tyr Ser Gln Ile Tyr Gly
                115                 120                 125

Trp Tyr Arg Val His Phe Gly Val Leu Asp Glu Gln Leu His Arg Asn
                130                 135                 140

Arg Gly Tyr Arg Asp Arg Tyr Tyr Ser Asn Leu Asp Ile Ala Pro Ala
```

```
            145                 150                 155                 160
Ala Asp Gly Tyr Gly Leu Ala Gly Phe Pro Pro Glu His Arg Ala Trp
                165                 170                 175

Arg Glu Glu Pro Trp Ile His His Ala Pro Pro Gly Ala Gly Asn Ala
                180                 185                 190

Pro Arg Ser Ser Gly Ser Thr Val Ala Thr Ala Pro Glu Val Lys Tyr
                195                 200                 205

Thr Val Phe Glu Thr Ala Leu Lys Gly Ser Gly Lys Thr Pro Glu Ala
                210                 215                 220

Asp Ala Gln Gln Asn Asn Phe Asn Lys Asp Gln Gln Ser Ala Phe Tyr
225                 230                 235                 240

Glu Ile Leu Asn Met Pro Asn Leu Asn Glu Ala Gln Arg Asn Gly Phe
                245                 250                 255

Ile Gln Ser Leu Lys Asp Asp Pro Ser Gln Ser Thr Asn Val Leu Gly
                260                 265                 270

Glu Ala Lys Lys Leu Asn Glu Ser Gln Ala Pro Lys Pro Glu Ala Asp
                275                 280                 285

Ala Gln Gln Asn Asn Phe Asn Lys Asp Gln Gln Ser Ala Phe Tyr Glu
    290                 295                 300

Ile Leu Asn Met Pro Asn Leu Asn Glu Ala Gln Arg Asn Gly Phe Ile
305                 310                 315                 320

Gln Ser Leu Lys Asp Asp Pro Ser Gln Ser Thr Asn Val Leu Gly Glu
                325                 330                 335

Ala Lys Lys Leu Asn Glu Ser Gln Ala Pro Lys Pro Glu Val Ala Gly
                340                 345                 350

Gln Asn

<210> SEQ ID NO 20
<211> LENGTH: 4
<212> TYPE: PRT
<213> ORGANISM: Artificial Sequence
<220> FEATURE:
<223> OTHER INFORMATION: Synthetic peptide motif

<400> SEQUENCE: 20

His Phe Phe Lys
1
```